(12) United States Patent
Young et al.

(10) Patent No.: US 8,715,745 B2
(45) Date of Patent: *May 6, 2014

(54) FUNGICIDAL COMPOSITIONS INCLUDING HYDRAZONE DERIVATIVES AND COPPER

(75) Inventors: David H Young, Carmel, IN (US); Steven Howard Shaber, Zionsville, IN (US); Gerald Shaber, legal representative, Woodbury, NY (US); Cruz Avila-Adame, Carmel, IN (US); Nneka T Breaux, Indianapolis, IN (US); James M Ruiz, Westfield, IN (US); Thomas L Siddall, Zionsville, IN (US); Jeffery D. Webster, New Palestine, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 85 days.

This patent is subject to a terminal disclaimer.

(21) Appl. No.: 13/144,686

(22) PCT Filed: Jan. 14, 2010

(86) PCT No.: PCT/US2010/021049
§ 371 (c)(1),
(2), (4) Date: Sep. 23, 2011

(87) PCT Pub. No.: WO2010/083314
PCT Pub. Date: Jul. 22, 2010

(65) Prior Publication Data
US 2012/0009274 A1    Jan. 12, 2012

Related U.S. Application Data

(60) Provisional application No. 61/144,560, filed on Jan. 14, 2009.

(51) Int. Cl.
*A01N 33/26*    (2006.01)
*A01N 59/20*    (2006.01)
*A01N 33/00*    (2006.01)
*A01N 59/00*    (2006.01)
*A01N 31/00*    (2006.01)
*A01N 31/04*    (2006.01)

(52) U.S. Cl.
CPC ............... *A01N 33/26* (2013.01); *A01N 59/20* (2013.01); *A01N 33/00* (2013.01); *A01N 59/00* (2013.01); *A01N 31/00* (2013.01); *A01N 31/04* (2013.01)
USPC ............. 424/604; 424/638; 514/500; 556/35; 564/149; 564/150

(58) Field of Classification Search
CPC ....... A01N 31/00; A01N 31/04; A01N 33/00; A01N 33/26; A01N 59/00; A01N 59/20
USPC ..................... 424/604, 638; 514/500; 556/35; 564/149, 150
See application file for complete search history.

(56) References Cited

U.S. PATENT DOCUMENTS

| | | | |
|---|---|---|---|
| 3,829,492 A | 8/1974 | Miller et al. | |
| 4,277,500 A | 7/1981 | Rusay | |
| 8,455,394 B2* | 6/2013 | Young et al. | 504/100 |
| 8,476,194 B2* | 7/2013 | Young et al. | 504/121 |
| 2007/0185113 A1 | 8/2007 | Faeh et al. | |
| 2012/0010075 A1* | 1/2012 | Young et al. | 504/101 |
| 2012/0148682 A1* | 6/2012 | Young et al. | 424/638 |

FOREIGN PATENT DOCUMENTS

| | | |
|---|---|---|
| DE | 196 17 863 | 10/1997 |
| EP | 1 164 126 | 12/2001 |
| EP | 1 172 355 | 1/2002 |
| EP | 1298129 | 4/2003 |
| WO | WO 01/66792 | 9/2001 |
| WO | WO 02/060858 | 8/2002 |
| WO | WO 2004/037816 | 5/2004 |
| WO | WO 2006/045096 | 4/2006 |
| WO | WO 2006/056752 | 6/2006 |
| WO | WO 2008/039641 | 4/2008 |
| WO | WO 2008/121602 | 10/2008 |

OTHER PUBLICATIONS

Richardson, "Chapter 5: Copper Fungicides/Bactericides"—Jul. 13, 2012 IDS Document FE.*
"Reregistration Eligibility Decision (RED) for Coppers"—Jul. 13, 2012 IDS Document FF.*
Mohsen Ismail M: "New Derivatives of 3,5-Dichlorosalicylaldehyde as Antimycotic Agents" Indian Journal of Pharmaceutical Sciences, Medknow Publication Pvt Ltd, IN, vol. 48, No. 5, Sep. 1, 1986, pp. 121-124, XP000926581, ISSN: 0250-474X.
Phaniband Mohammedshafi A et al: "Novel transition complexes of Co(11), Ni(II), Cu(11), and Zn(11) derived from 3-[p-(5-substituted salicylidiinehydrazinocarbonyl)]pheny Isydnone" Main Group Chemistry, Gordon and Breach Publishers, Basel, CH, vol. 7, No. 4, Dec. 1, 2008 , pp. 285-299, XP009137374ISSN: 1024-1221.
Ainscough et al: "Cytotoxicity of salicylaldehyde benzoylhydrazone analogs and their transition metal complexes: quantitative structure-activity relationships" Journal of Inorganic Biochemistry, New York, NY, US LNKD-DOI:10.1016/S0162-0134(99)00131-2, vol. 77, No. 3-4, Dec. 1, 1999, pp. 125-133, XP002906285.
N.M. Samus et al: "Synthesis and Antimicrobial Activity of the Complexes of 3d-Metals with Substituted Salicylaldehyde Benzoylhydrazones"Pharmaceutical Chemistry Journal, vol. 38, No. 7, 2004, pp. 27-29, XP002600088.
Mohan M et al: "Synthesis, Characterization and Antitumor Activity of Some Metal Complexes of 3- and 5- Substituted Salicylaldehyde 0- Hydroxybenzoylhydrazones"Inorganica Chimica Acta, Elsevier BV, NL LNKD- DOI:10.1016/S0020-1693(00)90726-6, vol. 152, No. 1, Jan. 1, 1988, pp. 25-36, XP0080386291SSN: 0020-1693.

(Continued)

*Primary Examiner* — Sean Basquill
(74) *Attorney, Agent, or Firm* — C. W. Arnett; Faegre Baker Daniels, LLP

(57) ABSTRACT

The present invention relates to the use of hydrazone compounds and copper for controlling the growth of fungi.

16 Claims, No Drawings

(56) References Cited

OTHER PUBLICATIONS

Database CA [Online] Chemical Abstracts Service, Columbus, Ohio, US; 1998, Levchenkov, S. I. et al: "Complexes of copper (II) nitrate with 5-R-salicylaldehyde acylhydrazones: structure and magnetic properties" XP002600084 retrieved from STN Database accession No. 1998:351101 ; & Russian Journal of Coordination Chemistry (Translation of Koordinatsionnaya Khimiya) ( 1998 ), 24(5), 332-336 CODEN: RJCCEY; ISSN: 1070-3284, 1998.

Database Caplus [Online] Chemical Abstracts Service, Columbus, Ohio, US; 1987, Chowdry Dinesh et al: "Studies on a few hydrazones as possible fungicidal agents" XP002600085 Database accession No. 1988:420157 ; & Hindustan Antibiotics Bulletin,vol. 29, No. 1-4, 1987, pp. 20-22.

Dave M P et al: "Preparation and Antitubercular Activity of Some 1-(4-Amino-3,5-DIBROM0)-2-Benzalhydrazine and 1-A4-(Phenylthioureido-3,5-Dibromobenzoyl)Ü-2- Substituted-Benzalhydrazin"Journal of the Indian Chemical Society, The Indian Chemical Society, Calcutta; IN, vol. 61, No. 7, Jul. 1, 1984 , p. 609-610, XP001181933 ISSN: 0019-4522.

Buu-Hoi Ng Ph et al: "Tuberculostatic Hydrazides and Their Derivatives"Journal of the Chemical Society, Chemical Society, Letchworth; GB LNKD- D01:10.1039/ JR9530001358, Jan. 1, 1953 , pp. 1358-1364, XP008078631ISSN: 0368-1769.

Bhat A K et al: "Chemotherapy of Fungus Infections: Part III—Alkyl or Aryl Thiosemicarbazones, Acid Hydrazones & Styryl Aryl Ketones of 5-Bromo- & 5-Nitro-salicylaldehydes"Indian Journal of Chemistry, Jodhpur, IN, vol. 10, Jul. 1, 1972 , pp. 694-698, XP000926582.

Singh N K et al: "Synthesis, characterization and biological activity of the complexes of manganese (III), cobalt (III), nickel (II), copper (II) and zinc (II) with salicylaldehyde thiobenzhdrazone" Indian Journal of Chemistry. Section A. Inorganic, Physical, Theoretical and Analytical, New Dehli, IN, vol. 40A, No. 10, Jan. 1, 2001, pp. 1064-1069, XP009136875 ISSN: 0376-4710.

Database Beilstein [Online] Beilstein Institute for Organic Chemistry, Frankfurt-Main, DE; 1974, El-Agamy et al: XP002600086 Database accession No. 503023; & Journal of Drug Research, vol. 6, No. 2, 1974, p. 131.

International Search Report of the International Searching Authority for PCT/US2010/021040, Sep. 13, 2010.

International Preliminary Report on Patentability and Written Opinion of the International Searching Authority for PCT/US2010/021040, Jul. 19, 2011.

International Search Report of the International Searching Authority for PCT/US2010/021043, Sep. 6, 2010.

International Preliminary Report on Patentability and Written Opinion of the International Searching Authority for PCT/US2010/021043, Jul. 19, 2011.

International Search Report of the International Searching Authority for PCT/US2010/021049, Aug. 31, 2010.

International Preliminary Report on Patentability and Written Opinion of the International Searching Authority for PCT/US2010/021049, Jul. 19, 2011.

Database CA [Online] Chemical Abstracts Service, Columbus, Ohio, US; Aug. 8, 2002, Tsutsumi, Seiji et al: "Preparation of N-(2-hydroxyphenylmethyl and 2-hydorxybenzylidene)hydrazine and —amine derivatives having Maillard reaction inhibitory activity" XP002596498 retrieved from STN Database accession No. 2002:594805 * abstract & WO 02/060858 A1 (Meiji Seika Kaisha, Ltd., Japan) Aug. 8, 2002.

International Search Report of the International Searching Authority for PCT/US2010/021051, Sep. 27, 2010.

International Preliminary Report on Patentability and Written Opinion of the International Searching Authority for PCT/US2010/021051, Jul. 19, 2011.

Xian H et al: "Preparation of 1,2-diacylbenzenes from o-hydroxyaryl ketone acylhydrazones using corss-linked polyastyrene-(iodoso diacetate)Ü" Synthetic Communications, Talor & Rancis Group, Philadelphia, PA LNKD-DOE:10.1081/SCC-100105117, vol. 31, No. 16, Jan. 1, 2001, pp. 2413-2418, XP001102733, ISSN: 0039-7911.

Chang-Zheng Zheng et al: "N'-[(E)-1-(5-Bromo-2-hydroxyphenyl)-ethyl idene]benzohydrazide" ACTA Crystallagraphica Section E, vol. E64, 2008, pp. 02487-SUP-7, XP002599411.

Gilles Ulrich et al: "Synthesis of Bisisoindolomethylene Dyes Bearing Anisole or Ethylthiophene Residues for Red and Near-IR Fluorescence" SYNLETT, No. 10, 2007, pp. 1517-1520, XP002599421.

Robert R. Moriarty: Synthesis of 1,2-Diacylbenzenes from o-Hydroxyaryl Ketone Acylhydrazones Using [(Diacyetoxy)iodo]benzene Synthesis, No. 3, Mar. 1993 (Feb. 1993), pp. 318-321, XP002599413.

M.A. Hapipah et al: "Synthesis, Structural Characterization, Electrochemical and Antimicrobial Studies of Complexes from the NO Ligating Schiff Bases of Furoic Acid Hydrazide" Malaysian Journal of Science, No. 23, 2004, pp. 119-127, XP002599414.

Database Registry [Online] Chemical Abstracts Service, Columbus, Ohio, US; Aug. 22, 2006, XP002595380 RN 903349-78-0.

Database Registry [Online] Chemical Abstracts Service, Columbus, Ohio, US; Aug. 19, 2003, XP002595378, RN 569333-84-2.

Database Registry [Online] Chemical Abstracts Service, Columbus, Ohio US; Aug. 6, 2003, XP002595379, RN 561280-90-8.

International Search Report of the International Searching Authority for PCT/US2010/021055, Oct. 8, 2010.

International Preliminary Report on Patentability and Written Opinion of the International Searching Authority for PCT/US2010/021055, Jul. 19, 2011.

International Search Report of the International Searching Authority for PCT/US2010/021057, Sep. 13, 2010.

International Preliminary Report on Patentability and Written Opinion of the International Searching Authority for PCT/US2010/021057, Jul. 19, 2011.

International Search Report of the International Searching Authority for PCT/US2010/021061, Sep. 9, 2010.

Johnson, D.K. et al., "Cytotoxic Chelators and Chelates 1. Inhibiation of DNA Synthesis in Cultured Roden and Human Cells by Aroylhydrazones and by a Copper(II) Complex of Salicylaldehyde Benzoyl Hydrazone," Inorganica Cimica Acta, 1982, vol. 67 pp. 159-165.

Gudasi, K.B. et al., "X-ray Crystal Structure of the N-(2-hydroxy-1-naphthalidene)phenylglycine Schiff base. Synthesis and Characterization of its Transition Metal Complexes" Transition Metal Chemistry, 2006, vol. 31 pp. 580-585.

Malhotra, Rajesh, et al. "Ligational Behavior of N-Substituted Acid Hydrazides Towrds Transition Metals and Potentiation of their Microbiocidal Activity," Journal of Inorganic Biochemistry, 1992, vol. 46 pp. 119-127.

Koh, L.L., et al., "Complexes of Salicylaldehyde Acylhydrazones: Cytotoxicity, QSAR and Crystal Structure of the Sterically Hindered t-butyl Dimer," Journal of Inorganic Biochemistry, 1998, vol. 72, pp. 155-162.

Slepenkin, Anatoly, et al., "Reversal of the Antichlamydial Activity of Putative Type III Secretion Inhibitors by Iron," Infection and Immunity, Jul. 2007, vol. 75, No. 7, pp. 3478-3489.

Rollas, Sevim and Küçükgüzel, Ş. Guniz, "Review: Biological Activities of Hydrazone Derivatives," Molecules, 2007, vol. 12, pp. 1910-1939.

Richardson, H.W., "Chapter 5: Copper Fungicides/Bactericides", Handbook of Cooper Compounds and Applications, pp. 93-122 Published by Marcel Dekker, Inc., New York 1997.

"Reregistration Eligibility Decision (RED) for Coppers," EPA 738-R-06-020, Jul. 2006.

Maxwell, J.R., et al. "Synthesis of 5-Aryl-2H-tetrazoles, 5-Aryl-sH-tetrazole-2-acetic Acids, and [(4-Phenyl-5-aryl-4H-1,2,4-triazol-3-yl)thio]acetic Acids as Possible Superoxide Scavengers and Antiinflammatory Agents" J. Med. Chem, 1984, vol. 27, pp. 1565-1570.

Dydio, P., et al., "Bishydrazide Derivatives of Isoindoline as Simple Anion Receptrs, "J. Org. Chem. 2009, vol. 74, pp. 1525-1530.

(56) References Cited

OTHER PUBLICATIONS

Katritzky, A.R., et al., "Synthesis of Aliphatic Hydroxyaryl Ketones or (Hetro)aryl Hydroxyaryl Kentones by Acylation of Organometallic Regents," Synthesis, 2007, No. 20, pp. 3141-3146.

Ahmed, M. et al., Allosteric Inhibition of [$^{125}$I] ET-1 Binding to $ET_A$ Receptors by Aldoxime and Hydroxamic Acid Derivatives, medicinal Chemistry, 2008, vol. 4, pp. 298-308.

Zhihua Sui and Mark J. Macielag, "A convenient Synthesis of 3,5-bis(trifluoromethyl)salicylic Acid," Synthetic Communications, vol. 27 No. 20, 3581-3590. 1997.

Xiao-Hui Gu, et al. "Design, Synthesis, and Monoamine Transporter Binding Site Affinities of Methoxy Derivatives of Indatraline," J. Med. Chem. 2000, vol. 43, pp. 4868-4876.

Stokker, G.E. et al., "2-(aminomethyl)phenols, a New Class of Saluretic Agents, 1. Effects of Nuclear Substitution," J. Med. Chem. 1980, vol. 23, pp. 1414-1427.

Nina U. Hofsløkken and Lars Skattebøl, "Convenient Method for the ortho-Formylation of Phenols," Acta Chemica Scandinavica, 1999, vol. 53, pp. 258-262.

Miller, J.A., "The Metal-Promoted Fries Rearrangement," J. Org. Chem., 1987, vol. 52, pp. 322-323.

Aruffo, A.A. et al., "Structural Studies of FE(III) and Cu(II) Complexes of Salicylaldehyde Benzoyl Hydrazone, a Synthetic Chelating Agent Exhibiting Diverse Biological Properties," Inorganic Cimica Acta, vol. 67, pp. L25-L27, 1982.

Sharma, M.P. et al "Synthesis and Antimicrobial Study of Some Hydrazone Metal Complexes," Proceedings of the National Academy of Sciences, India, 1991, Section A Part IV, vol. LXI, pp. 447-452.

Bradner W. Coursen and Hugh D. Sisler, "Effect of the Antibiotic, Cycloheximide, on the Metabolism and Growth of Saccharomyces Pastorianus, "American Journal o fBotany, 1960, vol. 47, pp. 541-549.

S.R. Colby, "Caclulating Synergistic and Antagonistic Responses of Herbicide Combinations," Weeds, 1967, vol. 15, pp. 20-22.

D.C. Erwin and H. Katznelson, "Studies on the nutrition of Phytophthora Cryptogea," Canadian Journal of Microbiology, vol. 7, pp. 15-25, 1961.

Ainscough, E.W., et al. "Antitumour copper(II) salicylaaldehyde benzoylhydrazone ($H_2$sb) complexes: physicochemical properties and the signle-crystal X-ray structures of [{Cu($H_2$sb)(CCI$_3$Co$_2$)$_2$}$_2$] and [{Cu(Hsb)CIO$_4$)C$_2$H$_5$)H)}$_2$] and the related salicylaldehyde acetylhydrazone ($H_2$sa) complex, [Cu(Has)CI($H_2$O)]•$H_2$0," Inorganica Chimica Acta vol. 267, pp. 27-38, 1998.

Tapas Ghosh, et al., "Synthesis, structure, solution chemistry and the electronic effect of para substituents on the vanadium center in a family of mixed-ligand [$V^V$O(ONO)(ON)] complexes," Inorganica Chimica Acta, vol. 360, pp. 1753-1761, 2007.

* cited by examiner

FUNGICIDAL COMPOSITIONS INCLUDING HYDRAZONE DERIVATIVES AND COPPER

CROSS-REFERENCE TO RELATED APPLICATIONS

This application claims the benefit of U.S. Provisional Application Ser. No. 61/144,560, filed Jan. 14, 2009, the disclosure of which is expressly incorporated herein by reference. This application is a national stage of PCT/US2010/021049, filed Jan. 14, 2010, the disclosure of which is expressly incorporated herein by reference.

FIELD OF THE INVENTION

The present disclosure relates to hydrazone compounds, optionally with and without copper, and their use as fungicides. The compounds of the present disclosure may offer protection against ascomycetes, basidiomycetes, deuteromycetes and oomycetes.

BACKGROUND

Copper is used to control the growth of organisms, especially microorganisms, in a variety of applications such as those described in the "Handbook of copper compounds and applications" edited by H. W. Richardson and published by Marcel Dekker, Inc. New York (1997), which is expressly incorporated by reference herein. These applications may include its use in agriculture to control a wide range of fungal and bacterial diseases of plants. Copper products may also be used as aquatic biocides in fresh or marine environments. Copper products may be used in antifouling applications and to control unwanted organisms in ponds and lakes based on the toxicity of copper towards algae, fungi, macrophytes and mollusks. Copper-based materials may also be used as wood preservatives and on other materials to inhibit fungal and bacterial growth. Other uses also include killing plant roots in sewer systems.

Ecological risk assessment studies have shown that copper products, which normally are applied at high use rates, may be toxic to birds, mammals, fish and other aquatic species ("Reregistration Eligibility Decision (RED) for Coppers", EPA 738-R-06-020, July 2006, which is expressly incorporated by reference herein). Thus, while copper is a highly useful agent for controlling the growth of undesirable organisms in different environments, it is desirable to minimize the amount of copper applied.

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

SUMMARY OF THE INVENTION

One embodiment of the present disclosure may include compounds of Formula I:

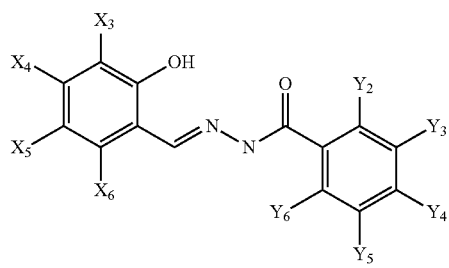

Formula 1 wherein R1 is H, C1-C4 alkyl, C3-C6 cycloalkyl, substituted aryl, substituted heteroaryl, C1-C4 haloalkyl, C3-C6 halocycloalkyl, unsubstituted aryl, and unsubstituted heteroaryl;

X3, X4, X5, and X6 are independently selected from the group consisting of H, halogen, nitro, cyano, C1-C4 alkyl, C1-C4 alkoxy, C2-C4 alkenyl, C2-C4 alkynyl, C1-C4 alkylthio, C1-C4 haloalkoxy, C2-C4 haloalkenyl, C2-C4 haloalkynyl, C1-C4 haloalkylthio, —SO$_2$R1, SONR1R1, —CR1=NOR1, —CONR1R1, NR1COOR1, —COOR1, substituted aryl, substituted heteroaryl, unsubstituted aryl, and unsubstituted heteroaryl; and Y2, Y3, Y4, Y5, and Y6 are independently selected from the group consisting of H, halogen, nitro, hydroxyl, cyano, C1-C4 alkyl, C1-C4 alkoxy, C2-C4 alkenyl, C2-C4 alkynyl, C1-C4 alkylthio, C1-C4 haloalkyl, C1-C4 haloalkoxy, C2-C4 haloalkenyl, C2-C4 haloalkynyl, C1-C4 haloalkylthio, —SO$_2$R1, SONR1R1, —CR1=NOR1, —CONR1R1, NR1COOR1, —COOR1, NR1R1, substituted aryl, substituted heteroaryl, unsubstituted aryl, unsubstituted heteroaryl, and phenoxy;

with the proviso that

X3 and X4, X4 and X5, X5 and X6, Y2 and Y3, or Y3 and Y4, may form a 5 or 6 membered fused ring which may contain up to two heteroatoms selected from the group consisting of O, N, and S;

at least one of X3, X4, X5, and X6 is Cl;

if X3 is Cl and X4, X5, and X6 are H, X5 is not Br;

if X5 is Cl and X4 and X6 are H, X3 is not H, Cl, Br, I, OCH3, OCH2CH3, or NO2;

if X3 is Cl and X4, X5, X6, Y2, Y3, Y5, and Y6 are H, Y4 is not Cl;

if X4 is Cl and X3, X5, and X6 are H, Y2, Y3, Y4, Y5, and Y6 are not all H;

if X4 is Cl and X3, X5, X6, Y2, Y3, Y5, and Y6 are H, Y4 is not hydroxyl;

if X4 is Cl and X3, X5, X6, Y3, Y4, Y5, and Y6 are H, Y2 is not hydroxyl;

if X4 is Cl and X3, X5, X6, Y2, Y4, Y5, and Y6 are H, Y3 is not F;

if X3, X4, X5, Y3, Y4, Y5, and Y6 are H and X6 is Cl, Y2 is not —NHCO;

if X3, X4, X5, Y3, Y4, Y5, and Y6 are H and X6 is Cl, Y4 is not methoxyphenyl;

if X4 is H and X5 and X6 are Cl, X3 is not OCH3 or OCH2CH3;

if X4, X6, Y3, Y4, Y5, and Y6 are H, X3 is Cl, and X5 is F, Y2 is not hydroxyl; and if X5 is Cl, X3 and X4 cannot combine to produce a substituted 8-hydroxyquinoline.

Another embodiment of the present disclosure may include a fungicidal composition for the control or prevention of fungal attack comprising the compounds described below and a phytologically acceptable carrier material.

Yet another embodiment of the present disclosure may include a method for the control or prevention of fungal attack on a plant, the method including the steps of applying a fungicidally effective amount of one or more of the compounds described below to at least one of the fungus, the plant, an area adjacent to the plant, and the seed adapted to produce the plant.

The term "alkyl" refers to a branched, unbranched, or cyclic carbon chain, including methyl, ethyl, propyl, butyl, isopropyl, isobutyl, tertiary butyl, pentyl, hexyl, cyclopropyl, cyclobutyl, cyclopentyl, cyclohexyl and the like.

The term "cycloalkyl" refers to a monocyclic or polycyclic, saturated substituent consisting of carbon and hydrogen.

The term "alkenyl" refers to a branched, unbranched or cyclic carbon chain containing one or more double bonds including ethenyl, propenyl, butenyl, isopropenyl, isobutenyl, cyclohexenyl, and the like.

The term "alkynyl" refers to a branched or unbranched carbon chain containing one or more triple bonds including propynyl, butynyl and the like.

As used throughout this specification, the term 'R' refers to the group consisting of C1-C4 alkyl, C2-C4 alkenyl, C2-C4 alkynyl, C3-C6 cycloalkyl, C1-C4 haloalkyl, C2-C4 haloalkenyl, C2-C4 haloalkynyl, or C3-C6 halocycloalkyl, unless stated otherwise.

The term "alkoxy" refers to an —OR substituent.

The term "alkylthio" refers to an —S—R substituent.

The term "haloalkylthio" refers to an alkylthio, which is substituted with Cl, F, I, or Br or any combination thereof.

The term "cyano" refers to a —C≡N substituent.

The term "hydroxyl" refers to an —OH substituent.

The term "haloalkoxy" refers to an —OR—X substituent, wherein X is Cl, F, Br, or I, or any combination thereof.

The term "haloalkyl" refers to an alkyl, which is substituted with Cl, F, I, or Br or any combination thereof.

The term "halocycloalkyl" refers to a monocyclic or polycyclic, saturated substituent consisting of carbon and hydrogen, which is substituted with Cl, F, I, or Br or any combination thereof.

The term "haloalkenyl" refers to an alkenyl, which is substituted with Cl, F, I, or Br or any combination thereof.

The term "haloalkynyl" refers to an alkynyl which is substituted with Cl, F, I, or Br or any combination thereof.

The term "halogen" or "halo" refers to one or more halogen atoms, defined as F, Cl, Br, and I.

The term "nitro" refers to a —$NO_2$ substituent.

The term "aryl" refers to a cyclic, aromatic substituent consisting of hydrogen and carbon.

The term "heteroaryl" refers to a cyclic substituent that may be fully unsaturated, where the cyclic structure contains at least one carbon and at least one heteroatom, where said heteroatom is nitrogen, sulfur, or oxygen.

Throughout the disclosure, reference to the compounds of Formula I is read as also including optical isomers and salts of Formula I, and hydrates thereof. Specifically, when Formula I contains a branched chain alkyl group, it is understood that such compounds include optical isomers and racemates thereof. Exemplary salts include: hydrochloride, hydrobromide, hydroiodide, and the like.

Certain compounds disclosed in this document can exist as one or more isomers. The various isomers include stereoisomers, geometric isomers, diastereomers, and enantiomers. Thus, the compounds disclosed in this invention include geometric isomers, racemic mixtures, individual stereoisomers, and optically active mixtures. It will be appreciated by those skilled in the art that one isomer may be more active than the others. The structures disclosed in the present disclosure are drawn in only one geometric form for clarity, but are intended to represent all geometric forms of the molecule.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or seeds.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

Additional features and advantages of the present invention will become apparent to those skilled in the art upon consideration of the following detailed description of the illustrative embodiments exemplifying the best mode of carrying out the invention as presently perceived.

DETAILED DESCRIPTION OF THE DISCLOSURE

The compounds of the present disclosure may be applied by any of a variety of known techniques, either as the compounds or as formulations comprising the compounds. For example, the compounds may be applied to the roots, seeds or foliage of plants for the control of various fungi, without damaging the commercial value of the plants. The materials may be applied in the form of any of the generally used formulation types, for example, as solutions, dusts, wettable powders, flowable concentrates, or emulsifiable concentrates.

The embodiments of the invention described herein are not intended to be exhaustive or to limit the invention to the precise forms disclosed. Rather, the embodiments selected for description have been chosen to enable one skilled in the art to practice the invention. Although the disclosure is described as a synergistic combination of copper, copper-based fungicides, or other copper-containing materials and a hydrazone or hydrazone derivative it should be understood that the concepts presented herein may be used in various applications and should not be limited.

The compounds of the present invention have fungitoxic activity against phytopathogenic fungi, against fungal pathogens of mammals, including humans, and against wood decay causing fungi. The compounds of the present invention may have broad spectrum fungitoxic activity, particularly against phytopathogenic fungi. They are active against fungi of a number of classes including Deuteromycetes (Fungi Imperfecti), Basidiomycetes, Oomycetes and Ascomycetes. More particularly, the method of this invention provides for activity against organisms including, but not limited to, *Phytophthora* species, *Plasmopara viticola, Pseudoperonospora cubensis, Pythium* species, *Pyricularia oryzae, Colletotrichum* species, *Helminthosporium* species, *Alternaria* species, *Septoria nodorum, Septoria tritici, Leptosphaeria nodorum, Ustilago maydis, Erysiphe graminis, Puccinia* species, *Sclerotinia* species, *Sphaerotheca fuliginea, Cercospora* species, *Rhizoctonia* species, *Uncinula necator* and *Podosphaera leucotricha*.

The method of the present invention also provides for activity against fungal pathogens of mammals (including humans) including, but not limited to, *Candida* species such as *C. albicans, C. glabrata, C. parapsilosis, C. krusei,* and *C. tropicalis, Aspergillus* species such as *Aspergillus fumigatus, Fusarium* species, *Coccidioides immitis, Cryptococcus neoformans, Histoplasma capsulatum, Microsporum* species, and *Tricophyton* species. The method of the present invention also provides for activity against fungi which cause wood decay such as *Gleophyllum trabeur, Phialophora mutabilis, Poria palcenta* and *Trametes versicolor*.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 10 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanool.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 5 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble pesticidally active ingredients emulsified in an aqueous vehicle at a concentration typically in the range from about 5 to about 50 weight percent, based on the total weight of the aqueous emulsion. If the pesticidally active ingredient is a solid it must be dissolved in a suitable water-immiscible solvent prior to the preparation of the aqueous emulsion. Emulsions are prepared by emulsifying the liquid pesticidally active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils. The formlulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

For pharmaceutical use, the compounds described herein may be taken up in pharmaceutically acceptable carriers, such as, for example, solutions, suspensions, tablets, capsules, ointments, elixirs and injectable compositions. Pharmaceutical preparations may contain from 0.1% to 99% by weight of active ingredient. Preparations which are in single dose form, "unit dosage form", preferably contain from 20% to 90% active ingredient, and preparations which are not in single dose form preferably contain from 5% to 20% active ingredient. As used herein, the term "active ingredient" refers to compounds described herein, salts thereof, and mixtures of compounds described herein with other pharmaceutically active compounds. Dosage unit forms such as, for example, tablets or capsules, typically contain from about 0.05 to about 1.0 g of active ingredient.

Suitable means of administering the pharmaceutical preparations include oral, rectal, topical (including dermal, buccal and sublingual), vaginal, parenteral (including subcutaneous, intramuscular, intravenous, intradermal, intrathecal and epidural) and by nasogastric tube. It will be understood by those skilled in the art that the preferred route of administration will depend upon the condition being treated and may vary with factors such as the condition of the recipient.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, isopyrazam, isotianil, kasugamycin, kasugamycin hydrochloride hydrate, kresoxim-methyl, mancopper, mancozeb, mandipropamid, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1- yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, 5-fluorocytosine and profungicides thereof, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, picolinamide UK-2A and derivatives thereof, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamide, IK-1140, and any combinations thereof.

The compounds of the present invention can also be combined with other antifungal compounds used to control infections in mammals to form fungicidal mixtures and synergistic mixtures thereof. The fungicidal compounds of the present invention can be applied in conjunction with one or more other antifungal compounds or their pharmaceutically acceptable salts to control a wider variety of undesirable diseases. When used in conjunction with other antifungal compounds, the presently claimed compounds can be formulated with the other antifungal compound(s), coadministered with the other antifungal compound(s) or applied sequentially with the other antifungal compound(s). Typical antifungal compounds include, but are not limited to compounds selected from the group consisting of an azole such as fluconazole, voriconazole, itraconazole, ketoconazole, and miconazole, a polyene such as amphotericin B, nystatin or liposomal and lipid forms thereof such as Abelcet, AmBisome and Amphocil, a purine nucleotide inhibitor such as 5-fluorocytosine, a polyoxin such as nikkomycin, and pneumocandin or echinocandin derivatives such as caspofungin and micofungin.

Additionally, the compounds of the present invention may be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank mixed with the other pesticide(s) or applied sequentially with the other pesticide(s). Typical insecticides include, but are not limited to: antibiotic insecticides such as allosamidin and thuringiensin; macrocyclic lactone insecticides such as spinosad and spinetoram; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dessicant insecticides such as boric acid, diatomaceous earth and silica gel; diamide insecticides such as chlorantraniliprole, cyantraniliprole and flubendiamide; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethyl-amine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, alpha-endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, isofenphos-methyl, methamidophos and propetamphos; phosphorodiamide insecticides such as dimefox, mazidox, mipafox and schradan; oxadiazine insecticides such as indoxacarb; oxadiazoline insecticides such as metoxadiazone; phthalimide insecticides such as dialifos, phosmet and tetramethrin; pyrazole insecticides such as tebufenpyrad, tolefenpyrad; phenylpyrazole insecticides such as acetoprole, ethiprole, fipronil, pyrafluprole, pyriprole and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, meperfluthrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tetramethylfluthrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetramic acid insecticides such as spirotetramat; tetronic acid insecticides such as spiromesifen; thiourea insecticides such as diafenthiuron; urea insecticides such as flucofuron and sulcofuron; and unclassified insecticides such as closantel, copper naphthenate, crotamiton, EXD, fenazaflor, fenoxacrim, hydramethylnon, isoprothiolane, malonoben, metaflumizone, nifluridide, plifenate, pyridaben, pyridalyl, pyrifluquinazon, rafoxanide, sulfoxaflor, triarathene and triazamate, and any combinations thereof.

Additionally, the compounds of the present invention may be combined with herbicides that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank mixed with the herbicide(s) or applied sequentially with the herbicide(s). Typical herbicides include, but are not limited to: amide herbicides such as allidochlor, beflubutamid, benzadox, benzipram, bromobutide, cafenstrole, CDEA, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flampropand flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; thioamide herbicides such as chlorthiamid; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; benzothiazole herbicides such as benzazolin; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glufosinate-P, glyphosate and piperophos; phenoxy herbicides such as bromofenoxim, clomeprop, 2,4-DEB, 2,4-DEP, difenopenten, disul, erbon, etnipromid, fenteracol and trifopsime; oxadiazoline herbicides such as methazole, oxadiargyl, oxadiazon; oxazole herbicides such as fenoxasulfone; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazole herbicides such as pyroxasulfone; benzoylpyrazole herbicides such as benzofenap, pyrasulfotole, pyrazolynate, pyrazoxyfen, and topramezone; phenylpyrazole herbicides such as fluazolate, nipyraclofen, pioxaden and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, indaziflam, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, ipfencarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as benzfendizone, bromacil, butafenacil, flupropacil, isocil, lenacil, saflufenacil and terbacil; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chlorreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, nicosulfuron, orthosulfamuron, oxasulfuron, primisulfuron, propyrisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, aminocyclopyrachlor, azafenidin, bentazone, benzobicyclon, bicyclopyrone, buthidazole, calcium cyanamide, cambendichlor, chlorfenac, chlorfenprop, chlorflurazole, chlorflurenol, cinmethylin, clomazone, CPMF, cresol, cyanamide, ortho-dichlorobenzene, dimepiperate, endothal, fluoromidine, fluridone, fluorochloridone, flurtamone, fluthiacet, indanofan, methyl isothiocyanate, OCH, oxaziclomefone, pentachlorophenol, pentoxazone, phenylmercury acetate, prosulfalin, pyribenzoxim, pyriftalid, quinoclamine, rhodethanil, sulglycapin, thidiazimin, tridiphane, trimeturon, tripropindan and tritac.

The compounds have broad ranges of efficacy as fungicides. The exact amount of the hydrazones and copper-containing materials to be applied is dependent not only on the specific active materials being applied and relative amounts of hydrazone and copper in the mixtures, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

Another embodiment of the present disclosure is a method for the control or prevention of fungal attack. This method comprises applying to the soil, plant, roots, foliage, seed or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact amount of a compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, g/m²).

For foliar control of fungal infections on plants, the amount of copper used in mixture with hydrazone may range from 0.001 to 5 kg/ha, and preferably from 0.05 to 1 kg/ha. The amount of hydrazone used in mixture with copper may range from 0.001 to 5 kg/ha, and preferably from 0.05 to 1 kg/ha. The molar ratio of copper to hydrazone may range from 0.1:1 to 10,000:1, preferably from 0.5:1 to 1000:1 and more preferably from 1:1 to 20:1.

It should be understood that the preferred amount of a copper material to be mixed with hydrazone in a given application may be influenced by availability of copper from other sources such as copper present in the soil or irrigation water, copper present on the foliage from natural sources, copper applied for fungal or bacterial disease control, copper applied as a fertilizer component, copper present in the water used in preparing fungicide solutions for application such as in spray application, copper present in formulations used in preparing spray solutions or dusts for application, or any other suitable copper source.

For fungal control the hydrazone may be applied before or after the application of copper such that the mixture is generated in the location where fungal control is desired. Additionally, multiple applications of copper or the hydrazone may be applied.

As a seed protectant, the amount of toxicant coated on the seed is usually at a dosage rate of about 10 to about 250 grams (g) and preferably from about 20 to about 60 g per 50 kilograms of seed. As a soil fungicide, the chemical can be incorporated in the soil or applied to the surface usually at a rate of 0.5 to about 20 kg and preferably about 1 to about 5 kg per hectare.

The compounds of the present invention may have broad spectrum fungitoxic activity, particularly against phytopathogenic fungi. They are active against fungi of a number of classes including Deuteromycetes (Fungi Imperfecti), Basidiomycetes, Oomycetes and Ascomycetes. More particularly, the method of this invention provides for activity against organisms including, but not limited to, *Phytophthora* species, *Plasmopara viticola, Pseudoperonospora cubensis, Pythium* species, *Pyricularia oryzae, Colletotrichum* species, *Helminthosporium* species, *Alternaria* species, *Septoria nodorum, Septoria tritici, Leptosphaeria nodorum, Ustilago maydis, Erysiphe graminis, Puccinia* species, *Sclerotinia* species, *Sphaerotheca fuliginea, Cercospora* species, *Rhizoctonia* species, *Uncinula necator* and *Podosphaera leucotricha*.

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures. Methods for preparation of salicylaldehyde benzoylhydrazones from salicylaldehydes or 2-hydroxyphenyl ketones and a benzoic hydrazide are well known in the literature. In addition the preparation of metal complexes of these materials is also well known (see for example *Journal of Inorganic Biochemistry* 1999, 77, 125-133 and *Inorganica Chimica Acta* 2007, 360, 1753-1761, which are expressly incorporated by reference herein). Methods of preparation of precursor hydrazides are also well known. Hydrazides can be prepared, for example, from carboxylic acids such as in Maxwell et al., *J. Med. Chem.* 1984, 27, 1565-1570, and from carboxylic esters such as in Dydio et al., *J. Org. Chem.* 2009, 74, 1525-1530, which are expressly incorporated by reference herein. Thus, the synthesis of any benzoylhydrazone of the present invention and its metal complex(es) is fully described where the starting aldehyde, and the starting benzoic hydrazide, acid, or ester are described. The hydrazones disclosed may also be in the form of pesticidally acceptable salts and hydrates. Example 4 below provides a typical method for the preparation of such benzoylhydrazones. Example 10 below provides a general method for the preparation of their metal complexes.

The following examples are presented to illustrate the various aspects of the compounds of the present disclosure and should not be construed as limitations to the claims.

Example 1

Preparation of 3,4-dichloro-2-hydroxybenzaldehyde

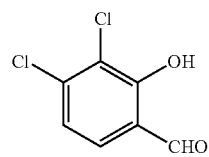 [SMILES: O=Cc1ccc(Cl)c(Cl)c1O]

3,4-Dichloro-2-hydroxybenzaldehyde was prepared from commercially available starting materials as described in Gu et al., *J. Med. Chem.* 2000, 43, 4868-4876, which is expressly incorporated by reference herein.

Example 2

Preparation of 3,6-dichloro-2-hydroxybenzaldehyde

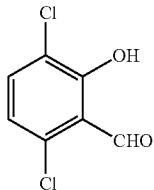 [SMILES: O=Cc1c(Cl)ccc(Cl)c1O]

3,6-Dichloro-2-hydroxybenzaldehyde was prepared from commercially available starting materials as described in Rafferty et al., PCT Int. Appl. WO 2008121602 A1, which is expressly incorporated by reference herein.

Example 3

Preparation of 2,3-dichloro-6-hydroxybenzaldehyde

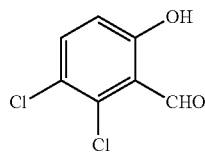 [SMILES: O=Cc1c(O)ccc(Cl)c1Cl]

2,3-Dichloro-6-hydroxybenzaldehyde was prepared from commercially available starting materials as described in Stokker et al., *J. Med. Chem.* 1980, 23, 1414-1427, which is expressly incorporated by reference herein.

Example 4

Preparation of 3-methyl-benzoic acid [1-(3-chloro-2-hydroxy-phenyl)-methylidene]-hydrazide

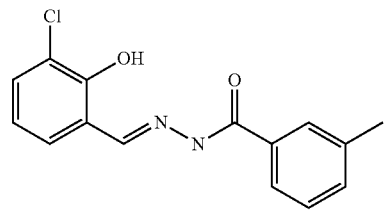 [SMILES: Cc1cccc(C(=O)N/N=C/c2cccc(Cl)c2O)c1]

A suspension of 3-chloro-2-hydroxy-benzaldehyde (0.100 g, 0.639 mmol) and 3-methyl-benzoic acid hydrazide (0.096 g, 0.639 mmol) in ethanol (2 mL) was heated to 60° C. for 18 hours. The reaction mixture was cooled to room temperature to precipitate the product. The solid was collected via suction filtration and rinsed with ethanol to furnish 3-methyl-benzoic acid [1-(3-chloro-2-hydroxy-phenyl)-methylidene]-hydrazide as a white solid (0.046 g, 25%): mp 166-169° C.; $^1$H NMR (400 MHz, CDCl$_3$) δ 8.59 (d, J=12.0 Hz, 1H), 7.76 (d, J=10.0 Hz, 2H), 7.47 (dd, J=15.6, 6.2 Hz, 4H), 6.97 (t, J=7.8 Hz, 1H), 2.39 (d, J=12.0 Hz, 3H); ESIMS m/z 289 ([M+H]$^+$), 287 ([M−H]$^-$).

TABLE 1

| Compound Number | Structure | mp (° C.) | ESIMS (+) | ESIMS (−) | $^1$H NMR (400 MHz, DMSO-d$_6$ unless otherwise stated), δ |
|---|---|---|---|---|---|
| 1 | 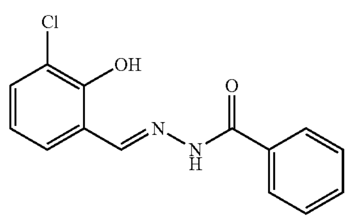 [SMILES: O=C(N/N=C/c1cccc(Cl)c1O)c1ccccc1] | 188-189 | 275 | 273 | 12.47 (s, 1H), 12.40 (s, 1H), 8.63 (s, 1H), 8.07-7.91 (m, 2H), 7.70-7.61 (m, 1H), 7.58 (t, J = 7.4 Hz, 2H), 7.50 (d, J = 7.9 Hz, 2H), 6.98 (t, J = 7.8 Hz, 1H) |
| 2 | 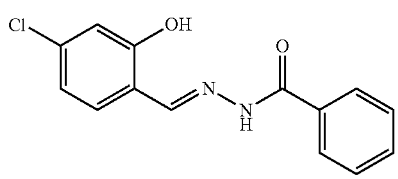 [SMILES: O=C(N/N=C/c1ccc(Cl)cc1O)c1ccccc1] | 218-219 | 275 | 273 | 12.16 (s, 1H), 11.60 (s, 1H), 8.65 (s, 1H), 7.95 (d, J = 7.2 Hz, 2H), 7.59 (dt, J = 14.8, 7.7 Hz, 4H), 7.10-6.83 (m, 2H) |
| 3 | 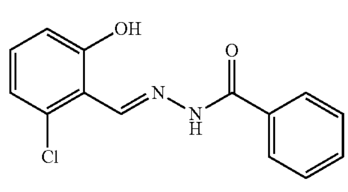 [SMILES: O=C(N/N=C/c1c(O)cccc1Cl)c1ccccc1] | 247-248 | 275 | 273 | 12.53 (s, 1H), 12.48 (s, 1H), 9.06 (s, 1H), 8.08-7.90 (m, 2H), 7.62 (dt, J = 28.8, 7.2 Hz, 3H), 7.34 (t, J = 8.2 Hz, 1H), 7.06 (dd, J = 7.9, 0.7 Hz, 1H), 6.97 (d, J = 8.3 Hz, 1H) |

TABLE 1-continued

| Compound Number | Structure | mp (° C.) | ESIMS (+) | ESIMS (−) | $^1$H NMR (400 MHz, DMSO-$d_6$ unless otherwise stated), δ |
|---|---|---|---|---|---|
| 4 | (3,4-dichloro-2-hydroxybenzylidene benzohydrazide) | 249-252 | 289 | 287 | 12.88 (s, 1H), 12.46 (s, 1H), 8.61 (s, 1H), 8.04-7.89 (m, 2H), 7.60 (ddd, J = 12.6, 11.5, 6.4 Hz, 4H), 7.23 (d, J = 8.4 Hz, 1H) |
| 5 | (4,5-dichloro-2-hydroxy-?-methylbenzylidene benzohydrazide) | 206-208 | 289 | 287 | 12.18 (s, 1H), 11.29 (s, 1H), 8.59 (s, 1H), 7.95 (dd, J = 11.2, 4.0 Hz, 2H), 7.69-7.47 (m, 4H), 6.94 (s, 1H), 2.30 (s, 3H) |
| 6 | (4,5-dichloro-2-hydroxybenzylidene benzohydrazide) | 238-241 | 309 | 307 | 12.25 (s, 1H), 11.61 (s, 1H), 8.62 (s, 1H), 8.08-7.71 (m, 2H), 7.68-7.29 (m, 4H), 7.19 (s, 1H) |
| 7 | (2,3-dichloro-6-hydroxybenzylidene benzohydrazide) | 273-274 | 309 | 307 | 12.76 (s, 1H), 12.55 (s, 1H), 9.06 (s, 1H), 8.09-7.90 (m, 2H), 7.62 (ddd, J = 22.7, 11.1, 7.0 Hz, 4H), 7.00 (d, J = 9.0 Hz, 1H) |
| 8 | (2,4-dichloro-6-hydroxybenzylidene benzohydrazide) | 273-274 | 309 | 307 | 12.92 (s, 1H), 12.52 (s, 1H), 8.98 (s, 1H), 8.09-7.88 (m, 2H), 7.73-7.52 (m, 3H), 7.22 (d, J = 2.0 Hz, 1H), 7.09 (d, J = 2.0 Hz, 1H) |
| 9 | (3,6-dichloro-2-hydroxybenzylidene benzohydrazide) | 204-205 | 309 | 307 | 13.45 (s, 1H), 12.61 (s, 1H), 9.02 (s, 1H), 7.99 (d, J = 7.3 Hz, 2H), 7.66 (t, J = 7.3 Hz, 1H), 7.59 (t, J = 7.5 Hz, 2H), 7.53 (d, J = 8.6 Hz, 1H), 7.09 (d, J = 8.6 Hz, 1H) |
| 10 | (3,4-dichloro-2-hydroxybenzylidene 3-methylbenzohydrazide) | 212-214 | 323 | 321 | 12.89 (s, 1H), 12.41 (s, 1H), 8.60 (s, 1H), 7.79-7.70 (m, 2H), 7.54 (d, J = 8.5 Hz, 1H), 7.45 (d, J = 4.4 Hz, 2H), 7.24 (d, J = 8.4 Hz, 1H), 2.41 (s, 3H) |
| 11 | (3,4-dichloro-2-hydroxybenzylidene 4-methylbenzohydrazide) | 254-256 | 323 | 321 | 12.92 (s, 1H), 12.39 (s, 1H), 8.60 (s, 1H), 7.87 (d, J = 8.1 Hz, 2H), 7.54 (d, J = 8.4 Hz, 1H), 7.38 (d, J = 8.1 Hz, 2H), 7.23 (d, J = 8.4 Hz, 1H), 2.40 (s, 3H) |

TABLE 1-continued

| Compound Number | Structure | mp (° C.) | ESIMS (+) | ESIMS (−) | ¹H NMR (400 MHz, DMSO-d$_6$ unless otherwise stated), δ |
|---|---|---|---|---|---|
| 12 | (3,4-dichloro-2-hydroxybenzylidene)-3-fluorobenzohydrazide | 215-218 | 327 | 325 | 12.75 (s, 1H), 12.50 (s, 1H), 8.61 (s, 1H), 7.81 (d, J = 7.8 Hz, 1H), 7.79-7.73 (m, 1H), 7.67-7.59 (m, 1H), 7.58 (d, J = 8.5 Hz, 1H), 7.51 (td, J = 8.4, 2.4 Hz, 1H), 7.24 (d, J = 8.4 Hz, 1H) |
| 13 | (3,4-dichloro-2-hydroxybenzylidene)-4-fluorobenzohydrazide | 244-246 | | 325 | 12.83 (s, 1H), 12.47 (s, 1H), 8.60 (s, 1H), 8.04 (dd, J = 8.7, 5.5 Hz, 2H), 7.56 (d, J = 8.5 Hz, 1H), 7.42 (t, J = 8.8 Hz, 2H), 7.24 (d, J = 8.4 Hz, 1H) |
| 14 | (3,4-dichloro-2-hydroxybenzylidene)-3-chlorobenzohydrazide | 219-222 | 343 | 341 | 12.73 (s, 1H), 12.52 (s, 1H), 8.60 (s, 1H), 8.00 (t, J = 1.8 Hz, 1H), 7.92 (d, J = 7.8 Hz, 1H), 7.74-7.69 (m, 1H), 7.61 (t, J = 7.9 Hz, 1H), 7.57 (d, J = 8.5 Hz, 1H), 7.24 (d, J = 8.4 Hz, 1H) |
| 15 | (3,4-dichloro-2-hydroxybenzylidene)-4-chlorobenzohydrazide | 260-262 | 343 | 341 | 12.79 (s, 1H), 12.51 (s, 1H), 8.60 (s, 1H), 7.98 (d, J = 8.5 Hz, 2H), 7.66 (d, J = 8.5 Hz, 2H), 7.57 (d, J = 8.5 Hz, 1H), 7.24 (d, J = 8.4 Hz, 1H) |
| 16 | (3,4-dichloro-2-hydroxybenzylidene)-3-nitrobenzohydrazide | 269-271 | | 352 | 12.70 (s, 2H), 8.79 (s, 1H), 8.65 (s, 1H), 8.50-8.46 (m, 1H), 8.42-8.37 (m, 1H), 7.88 (t, J = 8.0 Hz, 1H), 7.59 (d, J = 8.5 Hz, 1H), 7.25 (d, J = 8.4 Hz, 1H) |
| 17 | (3,4-dichloro-2-hydroxybenzylidene)-4-nitrobenzohydrazide | 237-243 | | 352 | 12.69 (s, 2H), 8.63 (s, 1H), 8.40 (d, J = 8.7 Hz, 2H), 8.19 (d, J = 8.7 Hz, 2H), 7.59 (d, J = 8.4 Hz, 1H), 7.24 (d, J = 8.4 Hz, 1H) |
| 18 | (3,4-dichloro-2-hydroxybenzylidene)-2-hydroxybenzohydrazide | 280-282 | 325 | 323 | 12.78 (s, 1H), 12.26 (s, 1H), 11.57 (s, 1H), 8.66 (s, 1H), 7.87 (dd, J = 7.9, 1.4 Hz, 1H), 7.54 (d, J = 8.5 Hz, 1H), 7.50-7.44 (m, 1H), 7.24 (d, J = 8.4 Hz, 1H), 7.03-6.96 (m, 2H) |

TABLE 1-continued

| Compound Number | Structure | mp (° C.) | ESIMS (+) | ESIMS (−) | ¹H NMR (400 MHz, DMSO-$d_6$ unless otherwise stated), δ |
|---|---|---|---|---|---|
| 19 | 3,4-dichloro-2-hydroxybenzaldehyde 2-(trifluoromethyl)benzoyl hydrazone | 209-213 | 377 | 375 | 12.56, 12.52, 12.41, 10.48 (4s, 2H), 8.47, 8.26 (2s, 1H), 7.92-7.59 (m, 4H), 7.57, 7.31 (2d, J = 8.5 Hz, 1H), 7.57, 7.31 (2d, J = 8.5 Hz, 1H); Note: rotational isomers |
| 20 | 3,4-dichloro-2-hydroxybenzaldehyde 2-hydroxy-4-methylbenzoyl hydrazone | 271-278 | 339 | 337 | 12.79 (s, 1H), 12.24 (s, 1H), 11.69 (s, 1H), 8.66 (s, 1H), 7.80 (d, J = 8.6 Hz, 1H), 7.54 (d, J = 8.5 Hz, 1H), 7.24 (d, J = 8.4 Hz, 1H), 6.84-6.79 (m, 2H), 2.31 (s, 3H) |
| 21 | 3,6-dichloro-2-hydroxybenzaldehyde 3-methylbenzoyl hydrazone | 214-216 | 323 | | 13.46 (s, 1H), 12.57 (s, 1H), 9.01 (s, 1H), 7.82-7.75 (m, 2H), 7.53 (d, J = 8.6 Hz, 1H), 7.49-7.45 (m, 2H), 7.10 (d, J = 8.6 Hz, 1H), 2.42 (s, 3H) |
| 22 | 3,6-dichloro-2-hydroxybenzaldehyde 4-methylbenzoyl hydrazone | 267-269 | 323 | 321 | 13.48 (s, 1H), 12.54 (s, 1H), 9.01 (s, 1H), 7.89 (d, J = 8.1 Hz, 2H), 7.52 (d, J = 8.6 Hz, 1H), 7.39 (d, J = 8.0 Hz, 2H), 7.09 (d, J = 8.6 Hz, 1H), 2.40 (s, 3H) |
| 23 | 3,6-dichloro-2-hydroxybenzaldehyde 3-fluorobenzoyl hydrazone | 203-209 | 327 | 325 | 13.35 (s, 1H), 12.65 (s, 1H), 9.01 (s, 1H), 7.83 (d, J = 7.8 Hz, 1H), 7.81-7.76 (m, 1H), 7.69-7.61 (m, 1H), 7.56-7.48 (m, 2H), 7.11 (d, J = 8.6 Hz, 1H) |
| 24 | 3,6-dichloro-2-hydroxybenzaldehyde 4-fluorobenzoyl hydrazone | 264-267 | 327 | 325 | 13.41 (s, 1H), 12.62 (s, 1H), 9.00 (s, 1H), 8.10-8.01 (m, 2H), 7.53 (d, J = 8.6 Hz, 1H), 7.44 (t, J = 8.8 Hz, 2H), 7.10 (d, J = 8.6 Hz, 1H) |
| 25 | 3,6-dichloro-2-hydroxybenzaldehyde 3-chlorobenzoyl hydrazone | 232-234 | 343 | 341 | 13.34 (s, 1H), 12.67 (s, 1H), 9.00 (s, 1H), 8.04-8.00 (m, 1H), 7.94 (d, J = 7.8 Hz, 1H), 7.74 (d, J = 9.0 Hz, 1H), 7.63 (t, J = 7.9 Hz, 1H), 7.54 (d, J = 8.6 Hz, 1H), 7.10 (d, J = 8.6 Hz, 1H) |

TABLE 1-continued

| Compound Number | Structure | mp (° C.) | ESIMS (+) | ESIMS (−) | $^1$H NMR (400 MHz, DMSO-$d_6$ unless otherwise stated), δ |
|---|---|---|---|---|---|
| 26 | 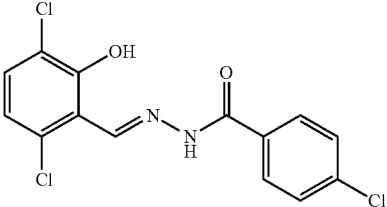 [SMILES: O=C(N/N=C/c1c(Cl)ccc(Cl)c1O)c1ccc(Cl)cc1] | 271-273 | 343 | | 13.38 (s, 1H), 12.66 (s, 1H), 9.00 (s, 1H), 8.00 (d, J = 8.5 Hz, 2H), 7.67 (d, J = 8.5 Hz, 2H), 7.53 (d, J = 8.6 Hz, 1H), 7.10 (d, J = 8.6 Hz, 1H) |
| 27 | 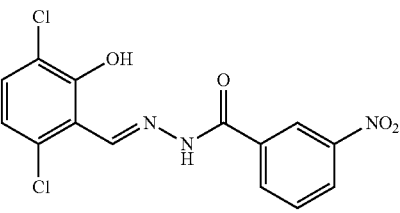 [SMILES: O=C(N/N=C/c1c(Cl)ccc(Cl)c1O)c1cccc([N+](=O)[O-])c1] | 273-277 | 354 | 352 | 13.33 (s, 1H), 12.91 (s, 1H), 9.03 (s, 1H), 8.84-8.81 (m, 1H), 8.50 (dd, J = 8.2, 1.4 Hz, 1H), 8.42 (d, J = 7.8 Hz, 1H), 7.90 (t, J = 8.0 Hz, 1H), 7.55 (d, J = 8.6 Hz, 1H), 7.12 (d, J = 8.6 Hz, 1H) |
| 28 | 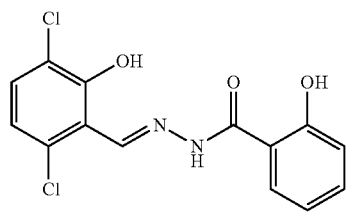 [SMILES: O=C(N/N=C/c1c(Cl)ccc(Cl)c1O)c1ccccc1O] | 260-262 | 325 | 323 | 13.43 (s, 1H), 12.46 (s, 1H), 11.48 (s, 1H), 9.06 (s, 1H), 7.86 (dd, J = 7.9, 1.6 Hz, 1H), 7.54 (d, J = 8.6 Hz, 1H), 7.52-7.45 (m, 1 H), 7.10 (d, J = 8.6 Hz, 1H), 7.05-6.96 (m, 2H) |
| 29 | 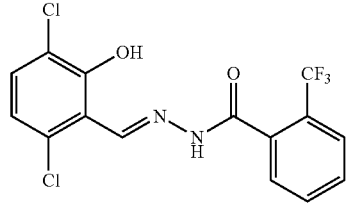 [SMILES: O=C(N/N=C/c1c(Cl)ccc(Cl)c1O)c1ccccc1C(F)(F)F] | 221-222 | 377 | 375 | 13.18, 12.73, 12.58, 10.82 (4s, 2H), 8.85, 8.65 (2s, 1H), 7.95-7.62 (m, 4H), 7.56, 7.44 (2d, J = 8.6 Hz, 1H), 7.11, 7.05 (2d, J = 8.6 Hz, 1H); Note: rotational isomers |
| 30 | 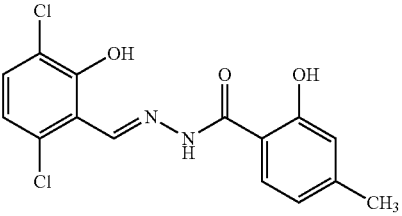 [SMILES: Cc1ccc(C(=O)N/N=C/c2c(Cl)ccc(Cl)c2O)c(O)c1] | 248-254 | 339 | 337 | 13.42 (s, 1H), 12.44 (s, 1H), 11.61 (s, 1H), 9.05 (s, 1H), 7.79 (d, J = 8.5 Hz, 1H), 7.53 (d, J = 8.6 Hz, 1H), 7.09 (t, J = 7.6 Hz, 1H), 6.85-6.81 (m, 2H), 2.32 (s, 3H) |
| 31 | 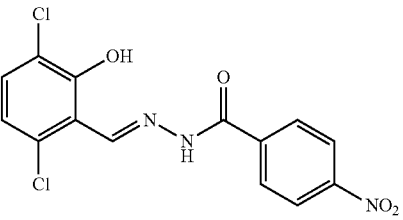 | 250-300 dec | 354 | 352 | 13.31 (s, 1H), 12.87 (s, 1H), 9.03 (s, 1H), 8.45-8.39 (m, 2H), 8.24-8.18 (m, 2H), 7.55 (d, J = 8.6 Hz, 1H), 7.11 (d, J = 8.6 Hz, 1H) |
| 32 | 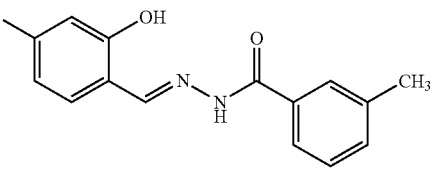 | 201-203 | 289 | 287 | 12.10 (s, 1H), 11.58 (s, 1H), 8.63 (s, 1H), 7.78-7.69 (m, 2H), 7.62 (d, J = 8.1 Hz, 1H), 7.43 (d, J = 4.7 Hz, 2H), 7.03-6.95 (m, 2H), 2.40 (s, 3H) |

TABLE 1-continued

| Compound Number | Structure | mp (° C.) | ESIMS (+) | ESIMS (−) | ¹H NMR (400 MHz, DMSO-$d_6$ unless otherwise stated), δ |
|---|---|---|---|---|---|
| 33 | 4-Cl, 2-OH benzylidene-N'-(4-methylbenzoyl)hydrazide | 258-260 | 289 | 287 | 12.09 (s, 1H), 11.62 (s, 1H), 8.63 (s, 1H), 7.85 (d, J = 8.1 Hz, 2H), 7.62 (d, J = 8.2 Hz, 1H), 7.35 (d, J = 8.0 Hz, 2H), 7.04-6.94 (m, 2H), 2.39 (s, 3H) |
| 34 | 4-Cl, 2-OH benzylidene-N'-(3-fluorobenzoyl)hydrazide | 218-222 | 293 | 291 | |
| 35 | 4-Cl, 2-OH benzylidene-N'-(4-fluorobenzoyl)hydrazide | 226-228 | 293 | 291 | 12.16 (s, 1H), 11.54 (s, 1H), 8.63 (s, 1H), 8.06-7.98 (m, 2H), 7.64 (d, J = 8.1 Hz, 1H), 7.44-7.35 (m, 2H), 7.03-6.95 (m, 2H) |
| 36 | 4-Cl, 2-OH benzylidene-N'-(3-chlorobenzoyl)hydrazide | 212-214 | | 307 | 12.20 (s, 1H), 11.45 (s, 1H), 8.64 (s, 1H), 8.01-7.96 (m, 1H), 7.90 (d, J = 7.8 Hz, 1H), 7.73-7.63 (m, 2H), 7.63-7.55 (m, 1H), 7.02-6.95 (m, 2H) |
| 37 | 4-Cl, 2-OH benzylidene-N'-(4-chlorobenzoyl)hydrazide | 257-260 | 309 | 307 | 12.20 (s, 1H), 11.50 (s, 1H), 8.64 (s, 1H), 7.96 (d, J = 8.5 Hz, 2H), 7.67-7.60 (m, 3H), 7.03-6.94 (m, 2H) |
| 38 | 4-Cl, 2-OH benzylidene-N'-(3-nitrobenzoyl)hydrazide | 233-238 | 320 | 318 | 12.41 (s, 1H), 11.42 (s, 1H), 8.81-8.77 (m, 1H), 8.69 (s, 1H), 8.46 (dd, J = 8.1, 1.8 Hz, 1H), 8.39 (d, J = 7.8 Hz, 1H), 7.86 (t, J = 8.0 Hz, 1H), 7.69 (d, J = 8.1 Hz, 1H), 7.04-6.96 (m, 2H) |
| 39 | 4-Cl, 2-OH benzylidene-N'-(4-nitrobenzoyl)hydrazide | 278-281 | 320 | 318 | 12.40 (s, 1H), 11.41 (s, 1H), 8.68 (s, 1H), 8.39 (d, J = 8.8 Hz, 2H), 8.18 (d, J = 8.8 Hz, 2H), 7.68 (d, J = 8.0 Hz, 1H), 7.03-6.96 (m, 2H) |
| 40 | 4-Cl, 2-OH benzylidene-N'-(2-hydroxybenzoyl)hydrazide | 210-213 | 291 | 289 | |

TABLE 1-continued

| Compound Number | Structure | mp (° C.) | ESIMS (+) | ESIMS (−) | $^1$H NMR (400 MHz, DMSO-$d_6$ unless otherwise stated), δ |
|---|---|---|---|---|---|
| 41 | 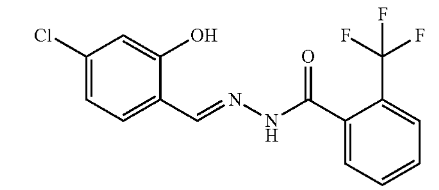 [SMILES: O=C(N/N=C/c1ccc(Cl)cc1O)c1ccccc1C(F)(F)F] | 197-200 | 343 | 341 | 12.20, 12.13, 11.27, 10.30 (4s, 2H), 8.47, 8.26 (2s, 1H), 7.90-7.16 (m, 5H), 7.01-6.80 (m, 2H); Note: rotational isomers |
| 42 | 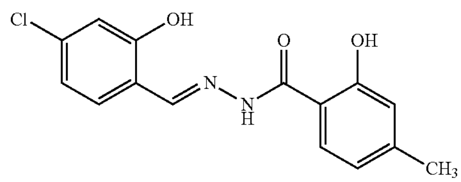 [SMILES: Cc1ccc(C(=O)N/N=C/c2ccc(Cl)cc2O)c(O)c1] | 283-287 | 305 | 303 | 12.02 (s, 1H), 11.90 (s, 1H), 11.51 (s, 1H), 8.67 (s, 1H), 7.81 (d, J = 8.5 Hz, 1H), 7.63 (d, J = 8.1 Hz, 1H), 7.04- 6.95 (m, 2H), 6.83-6.76 (m, 2H), 2.31 (s, 3H) |
| 43 | 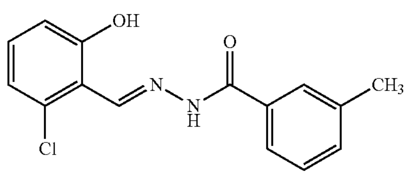 [SMILES: Cc1cccc(C(=O)N/N=C/c2c(O)cccc2Cl)c1] | 245-248 | 289 | 287 | 12.57 (s, 1H), 12.43 (s, 1H), 9.05 (s, 1H), 7.83-7.73 (m, 2H), 7.46 (d, J = 4.8 Hz, 2H), 7.34 (t, J = 8.2 Hz, 1H), 7.06 (dd, J = 7.9, 0.8 Hz, 1H), 6.96 (d, J = 8.3 Hz, 1H), 2.41 (s, 3H) |
| 44 | 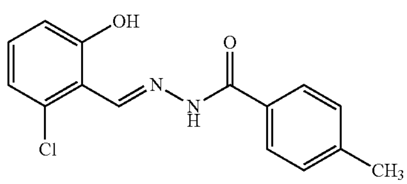 | 250-252 | 289 | 287 | 12.59 (s, 1H), 12.40 (s, 1H), 9.04 (s, 1H), 7.88 (d, J = 8.1 Hz, 2H), 7.38 (d, J = 8.0 Hz, 2H), 7.33 (t, J = 8.2 Hz, 1H), 7.06 (d, J = 8.0 Hz, 1H), 6.96 (d, J = 8.3 Hz, 1H), 2.40 (s, 3H) |
| 45 | 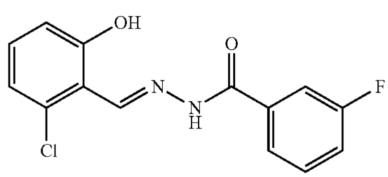 [SMILES: O=C(N/N=C/c1c(O)cccc1Cl)c1cccc(F)c1] | 257-259 | 293 | 291 | 12.52 (s, 1H), 12.48 (s, 1H), 9.04 (s, 1H), 7.83 (d, J = 7.8 Hz, 1H), 7.80-7.75 (m, 1H), 7.68-7.60 (m, 1H), 7.52 (td, J = 8.5, 2.4 Hz, 1H), 7.35 (t, J = 8.2 Hz, 1H), 7.07 (d, J = 7.9 Hz, 1H), 6.97 (d, J = 8.3 Hz, 1H) |
| 46 | 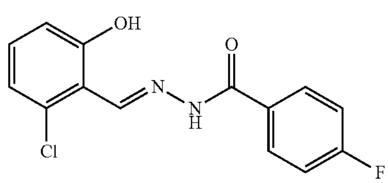 [SMILES: O=C(N/N=C/c1c(O)cccc1Cl)c1ccc(F)cc1] | 266-268 | 293 | 291 | 12.53 (s, 1H), 12.48 (s, 1H), 9.03 (s, 1H), 8.09-8.00 (m, 2H), 7.47-7.39 (m, 2H), 7.34 (t, J = 8.2 Hz, 1H), 7.06 (d, J = 7.8 Hz, 1H), 6.96 (d, J = 8.3 Hz, 1H) |
| 47 | 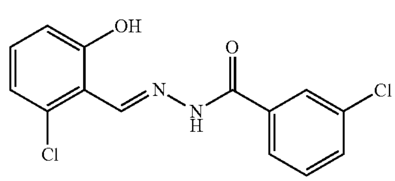 [SMILES: O=C(N/N=C/c1c(O)cccc1Cl)c1cccc(Cl)c1] | 250-253 | 309 | 307 | 12.54 (s, 1H), 12.47 (s, 1H), 9.04 (s, 1H), 8.05-7.98 (m, 1H), 7.96-7.90 (m, 1H), 7.76-7.69 (m, 1H), 7.62 (t, J = 7.9 Hz, 1H), 7.35 (t, J = 8.2 Hz, 1H), 7.07 (dd, J = 8.0, 1.0 Hz, 1H), 6.97 (d, J = 8.0 Hz, 1H) |
| 48 | 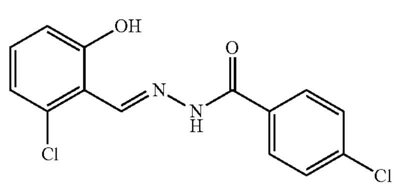 [SMILES: O=C(N/N=C/c1c(O)cccc1Cl)c1ccc(Cl)cc1] | 273-277 | 309 | 307 | 12.53 (s, 1H), 12.51 (s, 1H), 9.04 (s, 1H), 8.03-7.95 (m, 2H), 7.71-7.63 (m, 2H), 7.34 (t, J = 8.2 Hz, 1H), 7.07 (dd, J = 7.9, 0.9 Hz, 1H), 6.96 (d, J = 8.2 Hz, 1H) |

TABLE 1-continued

| Compound Number | Structure | mp (° C.) | ESIMS (+) | ESIMS (−) | $^1$H NMR (400 MHz, DMSO-d$_6$ unless otherwise stated), δ |
|---|---|---|---|---|---|
| 49 | (2-hydroxy-6-chlorobenzaldehyde 3-nitrobenzoyl hydrazone) | 269-270 | 320 | 318 | 12.77 (s, 1H), 12.48 (s, 1H), 9.07 (s, 1H), 8.82 (t, J = 1.9 Hz, 1H), 8.52-8.45 (m, 1H), 8.41 (d, J = 7.9 Hz, 1H), 7.89 (t, J = 8.0 Hz, 1H), 7.36 (t, J = 8.2 Hz, 1H), 7.08 (dd, J = 7.9, 0.8 Hz, 1H), 6.98 (d, J = 8.2 Hz, 1H) |
| 50 | (2-hydroxy-6-chlorobenzaldehyde 4-nitrobenzoyl hydrazone) | >300 | 320 | 318 | 12.73 (s, 1H), 12.44 (s, 1H), 9.06 (s, 1H), 8.46-8.38 (m, 2H), 8.25-8.16 (m, 2H), 7.36 (t, J = 8.2 Hz, 1H), 7.08 (dd, J = 8.0, 0.9 Hz, 1H), 6.97 (d, J = 8.1 Hz, 1H) |
| 51 | (2-hydroxy-6-chlorobenzaldehyde 2-hydroxybenzoyl hydrazone) | 277-280 | 291 | 289 | 12.52 (s, 1H), 12.37 (s, 1H), 11.55 (s, 1H), 9.07 (s, 1H), 7.86 (dd, J = 7.9, 1.5 Hz, 1H), 7.52-7.43 (m, 1H), 7.35 (t, J = 8.2 Hz, 1H), 7.07 (dd, J = 7.9, 0.9 Hz, 1H), 7.03-6.95 (m, 3H) |
| 52 | (2-hydroxy-6-chlorobenzaldehyde 2-trifluoromethylbenzoyl hydrazone) | 222-226 | 343 | 341 | 12.57, 12.45, 12.30, 10.21 (4s, 2H), 8.88, 8.64 (2s, 1H), 7.92-6.70 (m, 7H); Note: rotational isomers |
| 53 | (2-hydroxy-6-chlorobenzaldehyde 2-hydroxy-4-methylbenzoyl hydrazone) | 273-276 | 305 | 303 | 12.51 (s, 1H), 12.35 (s, 1H), 11.70 (s, 1H), 9.07 (s, 1H), 7.82-7.75 (m, 1H), 7.34 (t, J = 8.2 Hz, 1H), 7.09-7.03 (m, 1H), 6.96 (d, J = 8.3 Hz, 1H), 6.82 (d, J = 4.2 Hz, 2H), 2.32 (s, 3H) |
| 54 | (3-chloro-2-hydroxybenzaldehyde 3-methylbenzoyl hydrazone) | 166-169 | 289 | 287 | (400 MHz, CDCl$_3$) 8.59 (d, J = 12.0 Hz, 1H), 7.76 (d, J = 10.0 Hz, 2H), 7.47 (dd, J = 15.6, 6.2 Hz, 4H), 6.97 (t, J = 7.8 Hz, 1H), 2.39 (d, J = 12.0 Hz, 3H) |
| 55 | (3-chloro-2-hydroxybenzaldehyde 4-methylbenzoyl hydrazone) | 230-232 | 289 | 287 | (400 MHz, CDCl$_3$) 8.60 (s, 1H), 7.87 (d, J = 8.1 Hz, 2H), 7.49 (d, J = 7.9 Hz, 2H), 7.37 (d, J = 8.1 Hz, 2H), 6.97 (t, J = 7.8 Hz, 1H), 2.40 (s, 3H) |

TABLE 1-continued

| Compound Number | Structure | mp (° C.) | ESIMS (+) | ESIMS (−) | ¹H NMR (400 MHz, DMSO-d₆ unless otherwise stated), δ |
|---|---|---|---|---|---|
| 56 | 3-Cl, 2-OH benzaldehyde N'-(3-fluorobenzoyl)hydrazone | 178-184 | 293 | 291 | (400 MHz, CDCl₃) 8.62 (s, 1H), 7.86-7.72 (m, 2H), 7.63 (dd, J = 13.8, 8.0 Hz, 1H), 7.51 (dd, J = 7.1, 5.5 Hz, 3H), 6.98 (t, J = 7.8 Hz, 1H) |
| 57 | 3-Cl, 2-OH benzaldehyde N'-(4-fluorobenzoyl)hydrazone | 194-198 | 293 | 291 | (400 MHz, CDCl₃) 8.60 (s, 1H), 8.08-7.99 (m, 2H), 7.54-7.46 (m, 2H), 7.42 (t, J = 8.8 Hz, 2H), 6.98 (t, J = 7.8 Hz, 1H) |
| 58 | 3-Cl, 2-OH benzaldehyde N'-(3-chlorobenzoyl)hydrazone | 174-178 | 309 | 307 | (400 MHz, CDCl₃) 8.61 (s, 1H), 8.00 (t, J = 1.7 Hz, 1H), 7.95-7.68 (m, 2H), 7.61 (t, J = 7.9 Hz, 1H), 7.55-7.47 (m, 2H), 6.98 (t, J = 7.8 Hz, 1H) |
| 59 | 3-Cl, 2-OH benzaldehyde N'-(4-chlorobenzoyl)hydrazone | 217-219 | 309 | 307 | (400 MHz, CDCl3) 8.61 (s, 1H), 7.98 (d, J = 8.6 Hz, 2H), 7.66 (d, J = 8.6 Hz, 2H), 7.50 (ddd, J = 7.9, 4.5, 1.4 Hz, 2H), 6.98 (t, J = 7.8 Hz, 1H) |
| 60 | 3-Cl, 2-OH benzaldehyde N'-(3-nitrobenzoyl)hydrazone | 236-239 | 320 | 318 | (400 MHz, CDCl₃) 8.80 (t, J = 1.9 Hz, 1H), 8.66 (s, 1H), 8.52-8.36 (m, 2H), 7.88 (t, J = 8.0 Hz, 1H), 7.53 (ddd, J = 9.7, 7.9, 1.5 Hz, 2H), 6.99 (t, J = 7.8 Hz, 1H) |
| 61 | 3-Cl, 2-OH benzaldehyde N'-(4-nitrobenzoyl)hydrazone | 284-287 | 320 | 318 | (400 MHz, CDCl₃) 8.64 (s, 1H), 8.41 (d, J = 8.5 Hz, 2H), 8.19 (d, J = 8.6 Hz, 2H), 7.56-7.47 (m, 2H), 6.98 (t, J = 7.8 Hz, 1H) |
| 62 | 3-Cl, 2-OH benzaldehyde N'-(2-hydroxybenzoyl)hydrazone | 266-268 | 291 | 289 | (400 MHz, CDCl₃) 8.66 (s, 1H), 7.87 (dd, J = 7.9, 1.6 Hz, 1H), 7.54-7.42 (m, 3H), 6.98 (ddd, J = 7.8, 5.6, 3.9 Hz, 3H) |

TABLE 1-continued

| Compound Number | Structure | mp (° C.) | ESIMS (+) | ESIMS (−) | $^1$H NMR (400 MHz, DMSO-d$_6$ unless otherwise stated), δ |
|---|---|---|---|---|---|
| 63 | (structure: 3-chloro-2-hydroxybenzaldehyde hydrazone with 2-trifluoromethylbenzoyl) | 118-121 | 343 | 341 | (400 MHz, CDCl$_3$) 8.36 (d, J = 82.5 Hz, 1H), 7.95-7.24 (m, 6H), 6.92 (dt, J = 42.3, 7.9 Hz, 1H) |
| 64 | (structure: 3-chloro-2-hydroxybenzaldehyde hydrazone with 2-hydroxy-4-methylbenzoyl) | 258-266 | 305 | 303 | (400 MHz, CDCl$_3$) 8.66 (s, 1H), 7.80 (d, J = 8.6 Hz, 1H), 7.49 (dd, J = 7.9, 2.1 Hz, 2H), 6.98 (t, J = 7.8 Hz, 1H), 6.81 (d, J = 7.3 Hz, 2H), 2.31 (s, 3H) |

As exemplified below, hydrazones of the present invention, or their metal complexes, in a mixture with copper or in a mixture with inorganic or organic mono- or divalent copper salts or chelates (hereinafter referred to as "copper products") increase the biological potency of copper products, enabling comparable or improved efficacy at lower copper use rates. While not intending to be all-inclusive, copper products which may be mixed with the compounds of the present invention to provide enhanced potency may include the following: copper oxychloride, copper octanoate, copper ammonium carbonate, copper arsenate, copper oxysulfate, copper formate, copper propionate, copper oxyacetate, copper citrate, copper chloride, copper diammonium chloride, copper nitrate, copper carbonate, copper phosphate, copper pyrophosphate, copper disodium EDTA, copper diammonium EDTA, copper oxalate, copper tartrate, copper gluconate, copper glycinate, copper glutamate, copper aspartate, copper adipate, copper palmitate, copper stearate, copper caprylate, copper decanoate, copper undecylenate, copper neodecanoate, copper linoleate, copper oleate, copper borate, copper methanesulfonate, copper sulfamate, copper acetate, copper hydroxide, copper oxide, copper oxychloride-sulfate, copper sulfate, basic copper sulfate, copper-oxine, copper 3-phenylsalicylate, copper chloride hydroxide, copper dimethyldithiocarbamate, ammonium copper sulfate, copper magnesium sulfate, copper naphthenate, copper ethanolamine, chromated copper arsenate, ammoniacal copper arsenate, ammoniacal copper zinc arsenate, ammoniacal copper borate, Bordeaux mixture, copper zinc chromate, cufraneb, cupric hydrazinium sulfate, cuprobam, nano-copper materials, and copper didecyldimethylammonium chloride and where appropriate the hydrates of such compounds.

Salicylaldehyde benzoylhydrazones such as those of the current invention are known in the literature as chelators of metal cations (*Inorganica Chimica Acta* 1982, 67, L25-L27, which is expressly incorporated by reference herein), including copper. Antimicrobial activity has been reported for o-hydroxybenzaldehyde-N-salicyloylhydrazone and its copper, nickel and cobalt complexes towards *Staphylococcus aureus, Escherichia coli, Aspergillus niger* and *A. flavus* (*Proceedings of the National Academy of Sciences, India* 1991, Section A Part IV, Vol. LXI, pp. 447-452, which is expressly incorporated by reference herein). However, data in this report showed that the copper complex of o-hydroxybenzaldehyde-N-salicyloylhydrazone had a similar level of antimicrobial activity to that of o-hydroxybenzaldehyde-N-salicyloylhydrazone alone and the nickel and cobalt complexes, and provided no indication that salicylaldehyde benzoylhydrazones might show any synergistic antimicrobial effect in combination with copper.

Example 5

Effect of Copper on Fungitoxicity of Hydrazones Towards *Leptosphaeria nodorum*

In vitro fungitoxicity assays against *Leptosphaeria nodorum* (LEPTNO) were conducted using the liquid growth medium described by Coursen and Sisler (*American Journal of Botany* 1960, 47, 541-549) except that copper micronutrient, normally included as $CuSO_4$, was omitted. The medium, termed "copper-minus", was prepared by dissolving 10 g glucose, 1.5 g $K_2HPO_4$, 2 g $KH_2PO_4$ and 1 g $(NH_4)_2SO_4$ in 1 liter of deionized water and treating the solution with 0.5 g Chelex 100 resin (Bio-Rad Analytical grade, 50-100 mesh, sodium form, cat#142-2822) by stirring at room temperature for 1 h. $MgSO_4.7H_2O$ (0.5 g) was added, and stirring was continued for a further hour. Trace elements (minus $CuSO_4$), and vitamins described by Coursen and Sisler were added from concentrated stock solutions and the entire medium was sterilized by filtration. Medium containing copper was prepared by adding $CuCl_2.2H_2O$ to the copper-minus medium at 20 μM. Test compounds were dissolved in dimethylsulfoxide (DMSO) then dilutions in copper-minus and copper-plus growth media were prepared as 100 μL aliquots in flat-bottomed 96-well microtiter plates.

LEPTNO was grown on potato dextrose agar in 9 cm diameter petri dishes for 7 days. Sterile deionized water (20 mL) was added to a culture plate and spores suspended by scraping the surface gently with a sterile plastic loop. The resulting suspension was filtered through a double layer of sterile cheesecloth. Filtered spore suspension (5 mL) was centrifuged in a bench centrifuge at 2000 rpm for 2 min. The resulting spore pellet was resuspended in 10 mL sterile deionized water (which had been treated with Chelex 100 resin using 0.5 g resin per liter of water by stirring at room temperature for 1 h), and recentrifuged. The spores were resuspended in copper-minus medium, and the suspension adjusted to $2 \times 10^5$ spores per mL. Microtiter plates were inoculated with 100 µL of this spore suspension and the plates incubated at 25° C. for 72 h before assessing fungal growth by measuring light scattering in a NepheloStar plate reader. Growth inhibition was determined by comparing growth in the presence of test compound with growth in control wells lacking test compound.

Results for growth inhibition by test compounds in copper-plus medium ("% Inhn Plus Copper Observed") were compared with predicted values ("% Inhn Plus Copper Predicted") that were calculated using the formula set forth by S. R. Colby in *Weeds* 1967, 15, 20-22 based on results obtained for the same compounds in copper-minus medium ("% Inhn Minus Copper Observed") and the inhibition attributed to copper chloride alone, as determined by comparing growth in copper-minus and copper-plus media without any test compound across experiments. Data are presented in Table 2. Results illustrate that hydrazones and copper produce a synergistic fungitoxic effect towards LEPTNO.

Example 6

Efficacy of Hydrazones in Mixture with Copper Against Tomato Blight (*Phytophthora infestans*)

Hydrazone compounds at 50 ppm in combination with 50 µM $CuCl_2 \cdot 2H_2O$ were evaluated as prophylactic treatments applied 24 h before inoculation. Efficacy was determined based on percentage of disease control against tomato late blight (TLB), causal agent *Phytophthora infestans*. Treatments were arranged in a completely randomized design with 3 repetitions each. A pot with one tomato plant was considered as an experimental unit. Hydrazones were dissolved in acetone and re-suspended in water containing 0.01% Triton® X-100, 0.1% Atlox 4913 and 50 μM $CuCl_2.2H_2O$ to a final concentration of 10% acetone. All treatments were applied to run off 24 h before inoculation using a spin-table sprayer. Inoculation with an aqueous suspension of *P. infestans* sporangia was performed using a Delta painting sprayer. Percentage of disease control was determined 7 days after inoculation. Data are presented in Table 2, and illustrate the efficacy of hydrazones in mixture with copper for control of tomato late blight.

TABLE 2

| Compound Number | Concn. (μg/mL) | LEPTNO % Inhn. Minus Copper Observed | LEPTNO % Inhn. Plus Copper Observed | LEPTNO % Inhn. Plus Copper Predicted | TLB % Control |
|---|---|---|---|---|---|
| 1 | 0.05 | 0.0 | 98.5 | 7.1 | 81.3 |
| 2 | 0.05 | 5.6 | 98.1 | 12.3 | 88.1 |
| 3 | 0.05 | 3.5 | 97.0 | 10.4 | 88.1 |
| 4 | 0.05 | 0.5 | 97.6 | 7.5 | 92.5 |
| 5 | 0.05 | 0.1 | 97.8 | 7.2 | 66.1 |
| 6 | 0.05 | 0.0 | 98.1 | 7.1 | 74.6 |
| 7 | 0.05 | 0.5 | 97.0 | 7.5 | 62.7 |
| 8 | 0.05 | 6.9 | 98.0 | 13.5 | 78.0 |
| 9 | 0.05 | 10.1 | 94.0 | 16.5 | 84.7 |
| 10 | 0.05 | 18.4 | 95.4 | 24.2 | 98.0 |
| 11 | 0.05 | 19.6 | 89.8 | 25.3 | 87.0 |
| 12 | 0.05 | 18.6 | 98.0 | 24.4 | 93.0 |
| 13 | 0.05 | 56.7 | 97.4 | 59.7 | 93.0 |
| 14 | 0.05 | 12.7 | 98.3 | 18.9 | 100.0 |

TABLE 2-continued

| Compound Number | Concn. (μg/mL) | LEPTNO % Inhn. Minus Copper Observed | LEPTNO % Inhn. Plus Copper Observed | LEPTNO % Inhn. Plus Copper Predicted | TLB % Control |
|---|---|---|---|---|---|
| 15 | 0.05 | 41.4 | 97.3 | 45.6 | 92.0 |
| 16 | 0.05 | 17.6 | 96.9 | 23.4 | 97.0 |
| 17 | 0.05 | 3.3 | 96.4 | 10.2 | 97.0 |
| 18 | 0.05 | 11.1 | 97.2 | 17.4 | 97.0 |
| 19 | 0.05 | 4.3 | 94.7 | 11.1 | 92.0 |
| 20 | 0.05 | 8.4 | 95.8 | 14.9 | 97.0 |
| 21 | 0.05 | 13.8 | 95.6 | 19.9 | 95.0 |
| 22 | 0.05 | 14.2 | 96.6 | 20.3 | 100.0 |
| 23 | 0.05 | 13.1 | 97.9 | 19.2 | 95.0 |
| 24 | 0.05 | 0.0 | 96.9 | 7.1 | 98.0 |
| 25 | 0.05 | 7.0 | 95.5 | 13.6 | 98.0 |
| 26 | 0.05 | 3.5 | 97.5 | 10.4 | 91.0 |
| 27 | 0.05 | 12.6 | 96.1 | 18.8 | 98.0 |
| 28 | 0.05 | 15.1 | 97.4 | 21.1 | 98.0 |
| 29 | 0.05 | 0.0 | 97.3 | 7.1 | 90.0 |
| 30 | 0.05 | 11.1 | 98.2 | 17.4 | 98.0 |
| 31 | 0.05 | 7.2 | 98.2 | 13.7 | 90.0 |
| 32 | 0.05 | 13.5 | 96.9 | 19.6 | 87.0 |
| 33 | 0.05 | 17.2 | 98.1 | 23.1 | 61.0 |
| 34 | 0.05 | 7.7 | 97.6 | 14.2 | 95.0 |
| 35 | 0.05 | 4.2 | 97.5 | 11.0 | 95.0 |
| 36 | 0.05 | 6.0 | 96.9 | 12.7 | 92.0 |
| 37 | 0.05 | 15.8 | 97.9 | 21.8 | 46.0 |
| 38 | 0.05 | 4.3 | 96.1 | 11.1 | 73.0 |
| 39 | 0.05 | 8.0 | 95.9 | 14.6 | 71.0 |
| 40 | 0.05 | 8.2 | 93.9 | 14.8 | 76.0 |
| 41 | 0.05 | 0.0 | 95.5 | 7.1 | 49.0 |
| 42 | | NT | NT | NT | 6.7 |
| 43 | 0.05 | 5.4 | 94.7 | 12.1 | 98.0 |
| 44 | 0.05 | 5.8 | 97.1 | 12.5 | 88.0 |
| 45 | 0.05 | 0.5 | 97.9 | 7.6 | 96.0 |
| 46 | 0.05 | 0.0 | 94.8 | 7.1 | 98.0 |
| 47 | 0.05 | 0.0 | 95.2 | 7.1 | 100.0 |
| 48 | 0.05 | 0.0 | 97.3 | 7.1 | 97.0 |
| 49 | 0.05 | 0.0 | 94.9 | 7.1 | 97.0 |
| 50 | 0.05 | 2.8 | 96.2 | 9.7 | 98.0 |
| 51 | 0.05 | 6.7 | 96.1 | 13.3 | 98.0 |
| 52 | 0.05 | 0.0 | 92.0 | 7.1 | 70.0 |
| 53 | 0.05 | 8.4 | 79.7 | 14.9 | 94.0 |
| 54 | 0.05 | 0.8 | 98.0 | 7.9 | 98.0 |
| 55 | 0.05 | 22.3 | 97.0 | 27.8 | 100.0 |
| 56 | 0.05 | 17.5 | 97.6 | 23.4 | 95.0 |
| 57 | 0.05 | 34.8 | 97.3 | 39.5 | 98.0 |
| 58 | 0.05 | 26.1 | 97.9 | 31.3 | 98.0 |
| 59 | 0.05 | 44.1 | 98.4 | 48.1 | 97.0 |
| 60 | 0.05 | 10.4 | 97.4 | 16.8 | 94.0 |
| 61 | 0.05 | 16.6 | 98.2 | 22.5 | 100.0 |
| 62 | 0.05 | 8.5 | 95.1 | 15.0 | 91.0 |
| 63 | 0.05 | 0.0 | 95.9 | 7.1 | 72.0 |
| 64 | 0.05 | 10.8 | 97.8 | 17.2 | 100.0 |
| $CuCl_2$, 10 μM | | | 7.1 ± 6.0 | | |

Example 7

Effect of Copper on Fungitoxicity of Hydrazones Towards *Phytophthora capsici*

In vitro fungitoxicity assays against *Phytophthora capsici* were conducted using the asparagine-sucrose (AS) medium described in *Canadian Journal of Microbiology* 1961, 7, 15-25, except that copper micronutrient, normally included as $CuSO_4$, was omitted. The medium, termed "copper-minus AS", was prepared by dissolving 2 g asparagine, 0.43 g $KH_2PO_4$, 0.3 g $K_2HPO_4$, 0.4 mL of a 0.5 mg/mL thiamine-HCl solution and 15 g sucrose in 1 liter of deionized water and treating the solution with 0.5 g Chelex 100 resin (Bio-Rad Analytical grade, 50-100 mesh, sodium form, cat#142-2822) by stirring at room temperature for 1 h. The pH was adjusted to 6.4, then $MgSO_4.7H_2O$ (100 μg/mL), $FeSO_4.7H_2O$ (1

µg/mL), CaCl$_2$ (50 µg/mL), ZnSO$_4$.7H$_2$O (1 µg/mL), NaMoO$_4$.2H$_2$O (0.2 µg/mL) and MnCl$_2$.4H$_2$O (0.2 µg/mL) were added and the entire medium was sterilized by filtration. "Copper-plus AS" medium was prepared by adding CuCl$_2$.2H$_2$O to the copper-minus AS medium at 100 µM. Test compounds were dissolved in DMSO then dilutions in copper-minus AS and copper-plus AS media were prepared as 100 µL aliquots in flat-bottomed 96-well microtiter plates.

*Phytophthora capsici* was grown on petri plates, 9 cm in diameter, containing 15 mL V-8 agar, pH 7.0, containing 200 mL V-8 juice, 4 g CaCO$_3$, and 20 g agar per liter. Plates were inoculated with 7-mm plugs from a 1-week old culture, incubated at 25° C. in the dark for 3 days, and then placed under fluorescent lights for 4 days to induce sporulation. Zoospore release from sporangia was induced by adding 15 mL of sterile deionized water (which had been treated with Chelex 100 resin using 0.5 g resin per liter of water by stirring at room temperature for 1 h) to each plate, and incubating for 10 min at 25° C. followed by 20 min at 4° C. The plates were returned to 25° C. for 10 min and the aqueous suspension of released zoospores was recovered. The zoospore suspension was adjusted to $5 \times 10^4$ spores/mL by dilution into Chelex 100-treated water. Microtiter plates were inoculated with 100 µL of spore suspension and incubated at 25° C. for 48 h before assessing fungal growth by measuring light scattering in a NepheloStar plate reader. Growth inhibition was determined by comparing growth in the presence of test compound with growth in control wells lacking test compound.

Results for growth inhibition by test compounds in copper-plus AS medium ("% Inhn Plus Copper Observed") were compared with predicted values ("% Inhn Plus Copper Predicted") that were calculated using the formula set forth by S. R. Colby in Weeds (1967), 15, 20-22 based on results obtained for the same compounds in copper-minus AS medium ("% Inhn Minus Copper Observed") and the inhibition attributed to copper chloride alone, as determined by comparing growth in copper-minus AS and copper-plus AS media without any test compound across experiments. Data are presented in Table 3. Results illustrate that hydrazones and copper produce a synergistic fungitoxic effect towards *Phytophthora capsici*.

TABLE 3

| Compound Number | Concentration (µg/mL) | % Inhn Minus copper Observed | % Inhn Plus copper Observed | % Inhn Plus copper Predicted |
| --- | --- | --- | --- | --- |
| 20 | 0.050 | 0.0 | 23.2 | 4.5 |
| 25 | 0.050 | 0.0 | 44.5 | 4.5 |
| 50 | 0.050 | 0.6 | 85.9 | 5.1 |
| 58 | 0.050 | 9.1 | 88.6 | 13.2 |
| CuCl$_2$, 50 uM | | | 4.5 ± 7.9 | |

Example 8

Effect of Copper on Fungitoxicity of Hydrazones Towards *Ustilago maydis*

In vitro fungitoxicity assays against *Ustilago maydis* were conducted using the copper-minus medium described in Example 5. Medium containing copper was prepared by adding CuCl$_2$.2H$_2$O to the copper-minus medium at 20 µM. Test compounds were dissolved in dimethylsulfoxide (DMSO) at 200 µg/mL and 1 µL aliquots were added to two wells of flat-bottomed 96-well microtiter plates. Copper-minus medium (100 µL) was added to one of the wells and copper-plus medium to the second well. Control wells, included for each medium, received 1 uL DMSO and 100 µL of medium.

*Ustilago maydis* was grown in 50 mL potato dextrose broth with shaking at 25° C. for 24 h. A 10 mL aliquot of the culture was centrifuged at 2000 rpm for 2 min, resuspended in 10 mL of sterile Chelex 100-treated water, and centrifuged again. The spores were resuspended in copper-minus medium, and the suspension adjusted to a concentration of $1 \times 10^5$ spores per mL. Microtiter plate wells containing test compound of DMSO (control) as described above were inoculated with 100 µL of this spore suspension and the plates incubated at 25° C. for 48 h before assessing fungal growth by measuring light scattering in a NepheloStar plate reader. Growth inhibition was determined by comparing growth in the presence of test compound with growth in control wells lacking test compound.

Results for growth inhibition by test compounds at 1 µg/mL in copper-plus medium ("% Inhn Plus Copper Observed") were compared with predicted results ("% Inhn Plus Copper Predicted") that were calculated using the formula set forth by S. R. Colby in *Weeds* 1967, 15, 20-22 based on results obtained for the same compounds in copper-minus medium ("% Inhn Minus Copper Observed") and the inhibition attributed to copper chloride alone, as determined by comparing growth in copper-minus and copper-plus media without any test compound. Data are presented in Table 4. Results illustrate that hydrazones and copper produce a synergistic fungitoxic effect towards *Ustilago maydis*.

TABLE 4

| Compound Number | % Inhn. Minus copper Observed | % Inhn. Plus copper Observed | % Inhn. Plus copper Predicted |
| --- | --- | --- | --- |
| 20 | 65.5 | 92.9 | 69.6 |
| 25 | 3.1 | 93.6 | 14.7 |
| 50 | 9.6 | 90.0 | 20.4 |
| 58 | 34.3 | 89.3 | 42.1 |
| CuCl$_2$, 10 µM | | 11.9 | |

Example 9

Effect of Copper on Fungitoxicity of Hydrazones Towards *Septoria tritici*

In vitro fungitoxicity assays against *Septoria tritici* were conducted using the copper-minus medium described in Example 5. Medium containing copper was prepared by adding CuCl$_2$.2H$_2$O to the copper-minus medium at 2 µM. Test compounds were dissolved in dimethylsulfoxide (DMSO) at 10 µg/mL and 1 µL aliquots were added to two wells of flat-bottomed 96-well microtiter plates. Copper-minus medium (100 µL) was added to one of the wells and copper-plus medium to the second well. Control wells, included for each medium, received 1 uL DMSO and 100 µL of medium.

*Septoria tritici* isolate USA-184 was grown on potato dextrose agar at 18° C. under black lights for 3 days. A loopful of spores was transferred from the culture to a 15 mL tube containing 5 mL of sterile Chelex-treated water. The spores were centrifuged at 2000 rpm for 2 min, resuspended in 10 mL water, and centrifuged again. The spores were resuspended in copper-minus medium, and the suspension adjusted to a concentration of $1 \times 10^5$ spores per mL. Microtiter plate wells containing test compound of DMSO (control) as described above were inoculated with 100 µL of this spore suspension and the plates incubated at 25° C. for 90 h before assessing fungal growth by measuring light scattering in a NepheloStar plate reader. Growth inhibition was determined by comparing growth in the presence of test compound with growth in control wells lacking test compound.

Results for growth inhibition by test compounds at 0.05 μg/mL in copper-plus medium ("% Inhn Plus Copper Observed") were compared with predicted results ("% Inhn Plus Copper Predicted") that were calculated using the formula set forth by S. R. Colby in *Weeds* 1967, 15, 20-22 based on results obtained for the same compounds in copper-minus medium ("% Inhn Minus Copper Observed") and the inhibition attributed to copper chloride alone, as determined by comparing growth in copper-minus and copper-plus media without any test compound. In this experiment, copper chloride alone (1 μM) had no effect on growth. Data are presented in Table 5. Results illustrate that hydrazones and copper produce a synergistic fungitoxic effect towards *Septoria tritici*.

TABLE 5

| Compound Number | % Inhibition Minus copper Observed | % Inhibition Plus copper Observed | % Inhibition Plus copper Predicted |
|---|---|---|---|
| 20 | 22.4 | 93.7 | 22.4 |
| 25 | 9.3 | 93.2 | 9.3 |
| 50 | 18.8 | 89.9 | 18.8 |
| 58 | 43.8 | 96.7 | 43.8 |
| $CuCl_2$, 1 μM |  | 0 |  |

Example 10

Comparative Efficacy of Isolated Copper-Hydrazone Complexes and Parent Hydrazones Towards *Leptosphaeria nodorum*

Hydrazones and their isolated copper complexes were compared with respect to their in vitro fungitoxicity towards LEPTNO. Copper complexes of hydrazones were prepared by precipitation from ethanol with $CuCl_2.2H_2O$, at a 1:1 molar ratio, as described in general by Ainscough, Brodie, Dobbs, Ranford, and Waters (*Inorganica Chimica Acta* 1998, 267, 27-38, which is expressly incorporated by reference herein).

A general synthesis of 1:1 metal-hydrazone complexes is as follows. The starting salicylaldehyde benzoylhydrazone is dissolved (or suspended) in EtOH (generally 0.1 mmol hydrazone per mL solvent) and agitated at a temperature ranging from room temperature to 80° C. for 30 min. To this solution (or suspension) is added 1 equivalent of the metal salt (generally as a 1 M solution in EtOH). The mixture is agitated for a period ranging from 1 to 24 h at a temperature ranging from room temperature to 80° C. The metal-hydrazone complex generally precipitates during the reaction or upon cooling and is isolated by filtration, washed with EtOH and finally washed with $Et_2O$. In the instances where the complex does not precipitate, the solvent is removed and the resulting solid metal-hydrazone complex is washed with $Et_2O$. Properties of particular copper complexes of hydrazones are provided in Table 6 below.

TABLE 6

| Complex Number | Compound Number | Metal Salt | Ratio Hydrazone: Metal Salt | Description | mp (° C.) |
|---|---|---|---|---|---|
| 65 | 1 | $CuCl_2$•$2H_2O$ | 1:1 | olive green solid | 260-275 |
| 66 | 2 | $CuCl_2$•$2H_2O$ | 1:1 | olive green solid | 286-290 |
| 67 | 3 | $CuCl_2$•$2H_2O$ | 1:1 | olive green solid | 259-263 |
| 68 | 4 | $CuCl_2$•$2H_2O$ | 1:1 | olive green solid | 299-308 |
| 69 | 15 | $CuCl_2$•$2H_2O$ | 1:1 | olive green solid | 240-254 |
| 70 | 26 | $CuCl_2$•$2H_2O$ | 1:1 | olive green solid | 257-267 |
| 71 | 37 | $CuCl_2$•$2H_2O$ | 1:1 | olive green solid | 262-293 |
| 72 | 48 | $CuCl_2$•$2H_2O$ | 1:1 | olive green solid | 296-297 |
| 73 | 59 | $CuCl_2$•$2H_2O$ | 1:1 | olive green solid | 212-270 |

In vitro fungitoxicity assays were conducted using the copper-minus medium described in Example 5. Test compounds were dissolved in dimethylsulfoxide (DMSO) then dilutions in copper-minus medium were prepared as 100 μL aliquots in flat-bottomed 96-well microtiter plates. Microtiter plates were inoculated with 100 μL of spore suspension at a concentration of $2\times10^5$ spores per mL, prepared as in Example 5. The plates were incubated at 25° C. for 72 h before assessing fungal growth by measuring light scattering in a NepheloStar plate reader. Growth inhibition was determined by comparing growth in the presence of test compound with growth in control wells lacking test compound.

Results for growth inhibition by hydrazones and corresponding isolated copper complexes (each at 0.1 μg/mL) are shown in Table 7. The results illustrate that isolated copper complexes of hydrazones are much more fungitoxic than the corresponding hydrazones.

TABLE 7

| Complex Number | Compound Number | Metal Salt | Ratio* | Hydrazone % Inhibition | Complex % Inhibition |
|---|---|---|---|---|---|
| 65 | 1 | $CuCl_2$•$2H_2O$ | 1:1 | 10.7 | 98.0 |
| 66 | 2 | $CuCl_2$•$2H_2O$ | 1:1 | 8.4 | 96.8 |
| 67 | 3 | $CuCl_2$•$2H_2O$ | 1:1 | 4.7 | 94.9 |
| 68 | 4 | $CuCl_2$•$2H_2O$ | 1:1 | 20.0 | 97.5 |
| 69 | 15 | $CuCl_2$•$2H_2O$ | 1:1 | 24.1 | 98.0 |
| 70 | 26 | $CuCl_2$•$2H_2O$ | 1:1 | 23.1 | 97.5 |
| 71 | 37 | $CuCl_2$•$2H_2O$ | 1:1 | 22.8 | 75.8 |
| 72 | 48 | $CuCl_2$•$2H_2O$ | 1:1 | 12.1 | 93.9 |
| 73 | 59 | $CuCl_2$•$2H_2O$ | 1:1 | 29.9 | 97.3 |

*Molar ratio of hydrazone:copper used to prepare complexes.

The invention claimed is:

1. A mixture including a) a copper salt or a copper chelate and b) a compound of Formula 1:

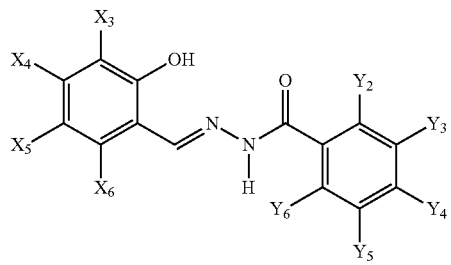

Formula 1 wherein
X3, X4, X5, and X6 are independently selected from the group consisting of H, halogen, nitro, cyano, C1-C4 alkyl, C1-C4 alkoxy, C2-C4 alkenyl, C2-C4 alkynyl, C1-C4 alkylthio, C1-C4 haloalkoxy, C2-C4 haloalkenyl, C2-C4 haloalkynyl, C1-C4 haloalkylthio, —SO$_2$R1, SONR1R1, —CR1=NOR1, —CONR1R1, NR1COOR1, —COOR1, substituted aryl, substituted heteroaryl, unsubstituted aryl, and unsubstituted heteroaryl;
Y2, Y3, Y4, Y5, and Y6 are independently selected from the group consisting of H, halogen, nitro, hydroxyl, cyano, C1-C4 alkyl, C1-C4 alkoxy, C2-C4 alkenyl, C2-C4 alkynyl, C1-C4 alkylthio, C1-C4 haloalkyl, C1-C4 haloalkoxy, C2-C4 haloalkenyl, C2-C4 haloalkynyl, C1-C4 haloalkylthio, —SO$_2$R1, SONR1R1, —CR1=NOR1, —CONR1R1, NR1COOR1, —COOR1, NR1R1, substituted aryl, substituted heteroaryl, unsubstituted aryl, unsubstituted heteroaryl, and phenoxy; and
R1 is H, C1-C4 alkyl, C3-C6 cycloalkyl, substituted aryl, substituted heteroaryl, C1-C4 haloalkyl, C3-C6 halocycloalkyl, unsubstituted aryl, or unsubstituted heteroaryl;
with the proviso that
X3 and X4, X4 and X5, X5 and X6, Y2 and Y3, or Y3 and Y4, may form a 5 or 6 membered fused ring which may contain up to two heteroatoms selected from the group consisting of O, N, and S;
at least one of X3, X4, X5, and X6 is Cl;
if X3 is Cl and X4, X5, and X6 are H, X5 is not Br;
if X5 is Cl and X4 and X6 are H, X3 is not H, Cl, Br, I, OCH3, OCH2CH3, or NO2;
if X3 is Cl and X4, X5, X6, Y2, Y3, Y5, and Y6 are H, Y4 is not Cl;
if X4 is Cl and X3, X5, and X6 are H, Y2, Y3, Y4, Y5, and Y6 are not all H;
if X4 is Cl and X3, X5, X6, Y2, Y3, Y5, and Y6 are H, Y4 is not hydroxyl;
if X4 is Cl and X3, X5, X6, Y3, Y4, Y5, and Y6 are H, Y2 is not hydroxyl;
if X4 is Cl and X3, X5, X6, Y2, Y4, Y5, and Y6 are H, Y3 is not F;
if X3, X4, X5, Y3, Y4, Y5, and Y6 are H and X6 is Cl, Y2 is not —NHCO;
if X3, X4, X5, Y3, Y4, Y5, and Y6 are H and X6 is Cl, Y4 is not methoxyphenyl;
if X4 is H and X5 and X6 are Cl, X3 is not OCH3 or OCH2CH3;
if X4, X6, Y3, Y4, Y5, and Y6 are H, X3 is Cl, and X5 is F, Y2 is not hydroxyl; and
if X5 is Cl, X3 and X4 cannot combine to produce a substituted 8-hydroxyquinoline.

2. A method for controlling the growth of fungal pathogens of plants comprising the step of: applying a fungicidally effective amount of a mixture of claim 1 to at least one of: soil, a plant, a part of a plant, foliage, and a seed.

3. A method for controlling the growth of fungal of mammals comprising the step of: contacting a mammal with a mixture of claim 1.

4. A method for controlling the growth of fungi on inert substrates comprising the step of: contacting an insert substance selected from the group consisting essentially of wood, metal, and plastic with a mixture of claim 1.

5. A method for controlling the growth of fungi comprising the step of: applying a mixture of claim 1 to a surface, wherein the fungi belong to at least one of Ascomycete, Basidiomycete, Oomycete, and Deuteromycete classes of fungi.

6. The mixture of claim 1 wherein the mixture has pesticidal activity against at least one organism selected from the group consisting of *Phytophthora* species, *Plasmopara viticola*, *Pseudoperonospora cubensis*, *Pythium* species, *Pyricularia oryzae*, *Colletotrichum* species, *Helminthosporium* species, *Alternaria* species, *Septoria nodorum*, *Leptosphaeria nodorum*, *Ustilago maydis*, *Erysiphe graminis*, *Puccinia* species, *Sclerotinia* species, *Sphaerotheca fuliginea*, *Cercospora* species, *Rhizoctonia* species, *Uncinula necator* and *Podosphaera leucotricha*.

7. The mixture of claim 1, wherein a growth inhibiting amount of a compound of Formula 1 in mixture with the copper salt or the copper chelate is provided as a mixture in which the total molar ratio of copper provided in the copper salt or the copper chelate to the compound of Formula 1 exceeds 1:1.

8. The mixture of claim 1, wherein a growth inhibiting amount of a compound of Formula 1 is provided as an isolated hydrazone-copper complex in which the molar ratio of the copper to the compound of Formula 1 is one of 1:1 and 1:2.

9. The mixture of claim 1, wherein the compound of Formula 1 to be combined with copper is complexed with a metal.

10. The mixture of claim 9, wherein the metal complexed with the compound of Formula 1 is selected from the group consisting of $Cu^+$, $Cu^{2+}$, $Fe^{2+}$, $Fe^{3+}$, $Zn^{2+}$, and $Mn^{2+}$.

11. The mixture of claim 1, wherein the copper salt or copper chelate is provided as at least one of the group consisting of copper oxychloride, copper octanoate, copper ammonium carbonate, copper arsenate, copper oxysulfate, copper formate, copper propionate, copper oxyacetate, copper citrate, copper chloride, copper diammonium chloride, copper nitrate, copper carbonate, copper phosphate, copper pyrophosphate, copper disodium EDTA, copper diammonium EDTA, copper oxalate, copper tartrate, copper gluconate, copper glycinate, copper glutamate, copper aspartate, copper adipate, copper palmitate, copper stearate, copper caprylate, copper decanoate, copper undecylenate, copper neodecanoate, copper linoleate, copper oleate, copper borate, copper methanesulfonate, copper sulfamate, copper acetate, copper hydroxide, copper oxide, copper oxychloride-sulfate, copper sulfate, basic copper sulfate, copper-oxine, copper 3-phenylsalicylate, copper chloride hydroxide, copper dimethyldithiocarbamate, ammonium copper sulfate, copper magnesium sulfate, coppernaphthenate, copper ethanolamine, chromated copper arsenate, ammoniacal copper arsenate, ammoniacal copper zinc arsenate, ammoniacal copper borate, Bordeaux mixture, copper zinc chromate, cufraneb, cupric hydrazinium sulfate, cuprobam, nano-copper materials, and copper didecyldimethylammonium chloride.

12. The mixture of claim 1, wherein:
R1 is H, C1-C4 alkyl, C3-C6 cycloalkyl, C1-C4 haloalkyl, or C3-C6 halocycloalkyl;
X3, X4, X5, and X6 are independently selected from the group consisting of H, halogen, nitro, cyano, C1-C4 alkyl, C1-C4 alkoxy, C2-C4 alkenyl, and C1-C4 alkylthio; and
Y2, Y3, Y4, Y5, and Y6 are independently selected from the group consisting of H, halogen, nitro, hydroxyl, cyano, C1-C4 alkyl, C1-C4 alkoxy, C1-C4 haloalkyl, C1-C4 haloalkoxy, C1-C4 alkylthio, —NR1R1, substituted aryl, unsubstituted aryl, and phenoxy;
with the proviso that X3 and X4, X5 and X6, or Y3 and Y4, may form a 5 or 6 membered fused ring which may contain up to two heteroatoms selected from the group consisting of O and N.

13. The mixture of claim 1, wherein:
X3, X4, X5, and X6 are independently selected from the group consisting of H, halogen, nitro, cyano, C1-C2 alkyl, C1-C2 alkoxy, C2-C3 alkenyl; and
Y2, Y3, Y4, Y5, and Y6 are independently selected from the group consisting of H, halogen, nitro, hydroxyl, cyano, C1-C4 alkyl, C1-C4 alkoxy, C1-C4 haloalkyl, and C1-C4 haloalkoxy;
with the proviso that Y3 and Y4 may form a 5 or 6 membered fused ring which may contain up to two heteroatoms selected from the group consisting of O and N.

14. The mixture of claim 1, wherein:
X3, X4, X5, and X6 are independently selected from the group consisting of H, halogen, nitro, C1-C4 alkyl, and C1-C4 alkoxy; and
Y2, Y3, Y4, Y5, and Y6 are independently selected from the group consisting of H, halogen, nitro, hydroxyl, methyl and trifluoromethyl.

15. The mixture of claim 1, wherein the copper salt or the copper chelate is a mono- or divalent copper salt or a mono- or divalent copper chelate.

16. The mixture of claim 6 wherein the pesticidal activity is synergistic.

* * * * *